US009629622B2

(12) United States Patent
Deland

(10) Patent No.: US 9,629,622 B2
(45) Date of Patent: *Apr. 25, 2017

(54) SUTURE GUIDE AND RUPTURED TISSUE REPAIR

(71) Applicant: Jonathan T. Deland, New York, NY (US)

(72) Inventor: Jonathan T. Deland, New York, NY (US)

( * ) Notice: Subject to any disclaimer, the term of this patent is extended or adjusted under 35 U.S.C. 154(b) by 548 days.

This patent is subject to a terminal disclaimer.

(21) Appl. No.: 13/845,475

(22) Filed: Mar. 18, 2013

(65) Prior Publication Data

US 2014/0094828 A1 Apr. 3, 2014

Related U.S. Application Data

(60) Continuation of application No. 12/614,764, filed on Nov. 9, 2009, now Pat. No. 8,398,661, which is a division of application No. 11/738,775, filed on Apr. 23, 2007, now Pat. No. 7,615,062, which is a continuation-in-part of application No. PCT/US2005/038490, filed on Oct. 25, 2005.

(60) Provisional application No. 60/621,720, filed on Oct. 25, 2004, provisional application No. 60/745,673, filed on Apr. 26, 2006.

(51) Int. Cl.
*A61B 17/04* (2006.01)

(52) U.S. Cl.
CPC .............. *A61B 17/0482* (2013.01)

(58) Field of Classification Search
CPC ............ A61B 17/0469; A61B 17/0482; A61B 17/17–17/1796; D05B 83/00; D05B 55/06
USPC ..... 112/227, 261; 606/96–98, 139, 144–150, 606/232
See application file for complete search history.

(56) References Cited

U.S. PATENT DOCUMENTS

| 4,465,065 A * | 8/1984 | Gotfried ........................ 606/65 |
| 5,078,719 A * | 1/1992 | Schreiber ....................... 606/87 |
| 5,098,383 A * | 3/1992 | Hemmy et al. ................ 604/116 |
| 6,036,700 A * | 3/2000 | Stefanchik et al. .......... 606/144 |
| 6,200,327 B1 * | 3/2001 | Assal ............................. 606/148 |
| 2004/0102788 A1 * | 5/2004 | Huebner et al. ................ 606/96 |
| 2006/0149250 A1 * | 7/2006 | Castaneda et al. ............. 606/69 |
| 2009/0149861 A1 * | 6/2009 | Brodsky et al. ................ 606/96 |

* cited by examiner

*Primary Examiner* — Elizabeth Houston
*Assistant Examiner* — Charles Wei
(74) *Attorney, Agent, or Firm* — Foley Hoag LLP

(57) ABSTRACT

A suture guide may include a base, a tissue guard extending from the base, and two flanking posts affixed to the base on opposite sides of the tissue guard. The posts may extend from the base in parallel planes, and each of the posts may define a plurality of channels passing through its width. The channels may be so oriented that, for each post (a) the channels define suture needle guide paths in one or more planes, and (b) at least one channel is not perpendicular to a long axis of the first flanking post, so that it defines an oblique suture needle guide path. The tissue guard may be connected to the base by a connector so adjustable as to control spacing between the posts and the tissue guard.

16 Claims, 27 Drawing Sheets

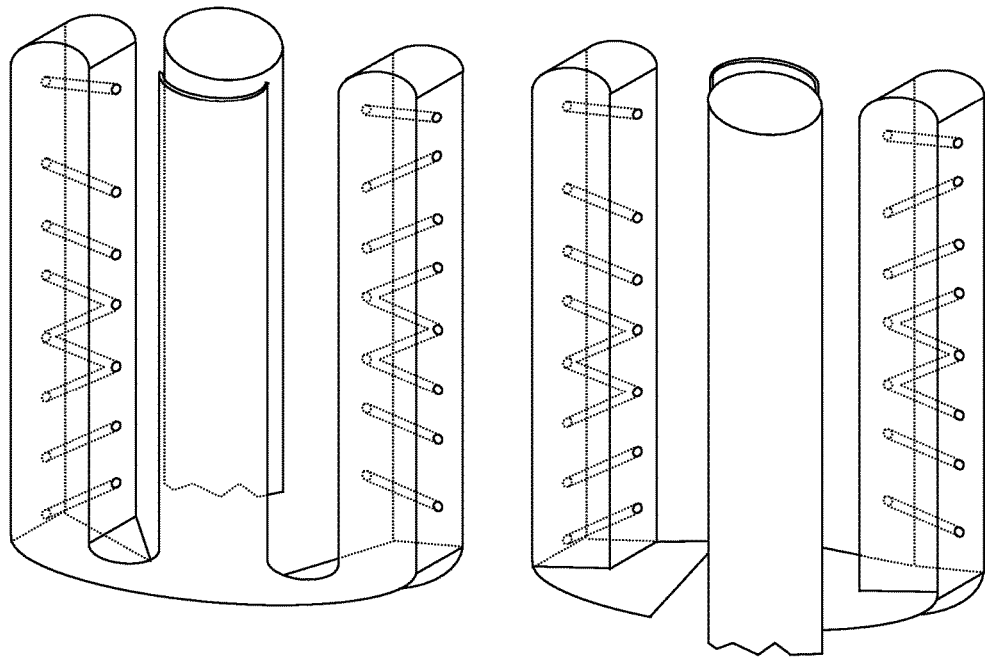
*FIG. 4*  *FIG. 5*

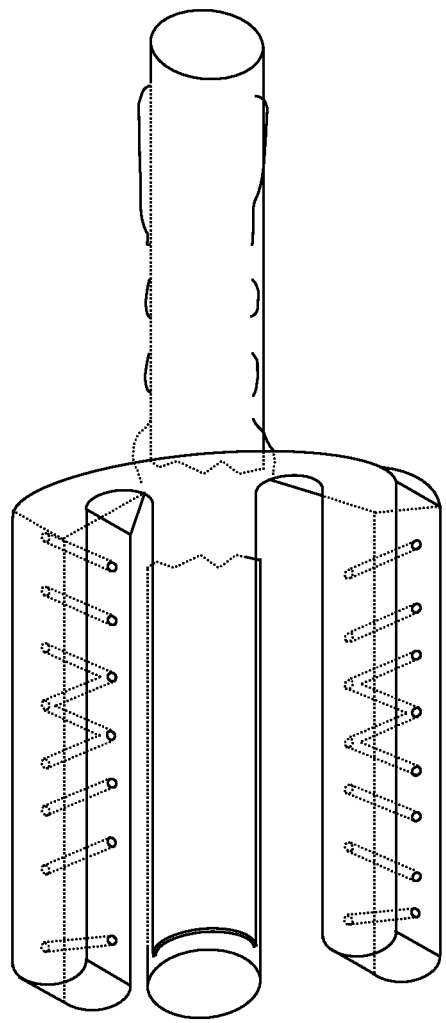 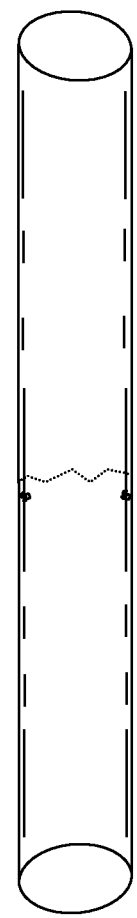
*FIG. 31*  *FIG. 32*

SUTURE GUIDE AND RUPTURED TISSUE REPAIR

CROSS-REFERENCE TO RELATED APPLICATIONS

This application is a continuation of U.S. application Ser. No. 12/614,764, filed Nov. 9, 2009, which is division of U.S. application Ser. No. 11/738,775, filed Apr. 23, 2007, which is a continuation-in-part of PCT/US05/038490, filed Oct. 25, 2005, which claims the benefit of U.S. Provisional Application No. 60/621,720, filed Oct. 25, 2004, both of which applications are hereby incorporated herein by reference. U.S. application Ser. No. 11/738,775 also claims the benefit of U.S. Provisional Application 60/745,673, filed Apr. 26, 2006, which is hereby incorporated herein by reference.

BACKGROUND

Tendon rupture is a debilitating event that limits motion and can cause pain. Rupture can result from overexertion, trauma, and age-related degeneration, among other causes. Surgical repair of the ruptured tendon is typically required; tendinous tissue has poor wound-healing properties, and the torn ends of the tendon separate from one other due to contraction of the unrestrained muscle attached to one tendon end.

Surgical repair of a ruptured tendon is typically performed by putting one or more sutures through each torn end and then sewing the complementing sutures to one another, thereby winching the torn ends together and restoring the connected muscle to its normal resting length. Two risks of tendon repair include inadequate strength of the repair and potential soft tissue problems from surgical exposure. Accordingly, it would be best if a tendon could be repaired through a small incision but with a strong repair. With a small incision, the needles used to advance the sutures through the tendon may be advanced manually, without any guides, but this practice risks placing the sutures unevenly, so that the tendon's natural geometry and strength are not restored, and the repair is weak. One approach, described in U.S. Pat. No. 6,200,327 to Assal, provides a two-piece guide member with aligned channels in each piece. The aligned channels allow a user to advance a loaded needle horizontally through the tendon in a precise and repeatable fashion. However, the structure of the Assal device necessarily limits each suture to just one pass through the tendon; this results in a potentially weak stitch that provides a minimum of surface area for the suture to engage the tendon.

SUMMARY

The present disclosure describes the structure and use of various suture guides that facilitate the precise and reproducible placement of multiple passes of a suture through a tissue.

A suture guide may include a tissue guard and a flanking post disposed to one side of the tissue guard. The flanking post may define a plurality of channels passing through its width. The channels may be so oriented that they define suture needle guide paths in one or more planes that do not intersect the tissue guard.

A suture guide may include a tissue guard and a flanking post disposed to one side of the tissue guard. The flanking post may define a plurality of channels passing through its width. The channels may be so oriented that they define suture needle guide paths in one or more planes that do not intersect the tissue guard, and so that at least one channel is not perpendicular to the long axis of the flanking post, so that it defines an oblique suture needle guide path.

A suture guide may include a tissue guard and two flanking posts disposed to opposite sides of the tissue guard. Each flanking post may define a plurality of channels passing through its width. The channels may be so oriented that they define suture needle guide paths in one or more planes that do not intersect the tissue guard.

A suture guide may include a tissue guard and a flanking post disposed to one side of the tissue guard. The flanking post may define one or more channels passing through its width. The channel may be so oriented that it defines a suture needle guide path in a plane that does not intersect the tissue guard. The guide may include a second flanking post that also defines one or more channels passing through its width. The channel of the second flanking post may be so oriented that it defines a suture needle guide path in a plane that does not intersect the tissue guard. The channel of the first flanking post and the channel of the second flanking post may define guide paths in the same plane.

A suture guide may include a tissue guard and a flanking post disposed to one side of the tissue guard. The flanking post may define a plurality of channels passing through its width. The channels may be so oriented that a) the channels define suture needle guide paths in one or more planes that do not intersect the tissue guard; and b) at least one channel is perpendicular to the long axis of the flanking post, so that it defines a horizontal suture needle guide path. All channels defined by the flanking post may be perpendicular to the long axis of the flanking post.

A method of suturing a tissue may include positioning a suture guide disclosed herein against a tissue to be sutured, so that the tissue guard overlies or supports the tissue and the flanking post flanks a first side of the tissue. A first needle, with a first suture attached, may be advanced through a needle guide path in the post and then the tissue, so that ends of the first suture emerge from the first side and a second side of the tissue. A second needle, with a second suture attached, may be advanced through a needle guide path in the post and then the tissue, forming a needle track, so that ends of the second suture emerge from the first side and the second side of the tissue. The sutures may be detached from their respective needles. The first suture may be attached to the end of the second suture that is on the second side of the tissue. The second suture may be retracted through the needle track, thereby pulling the first suture through the needle track and disposing its end on the first side of the tissue.

BRIEF DESCRIPTION OF THE DRAWINGS

FIGS. 1-5, 11-13, and 16 show perspective views of various exemplary embodiments of suture guides.

FIGS. 18-34 depict exemplary uses of an embodiment of a suture guide.

DETAILED DESCRIPTION

The suture guides disclosed herein provide suture needle guide paths that assist a surgeon or other user in positioning stitches in a precise and reproducible way. In particular, the disclosed suture guides include needle guide paths that allow the user to create multiple passes of a stitch through a tissue, which are stronger than a single pass.

Figure 1:
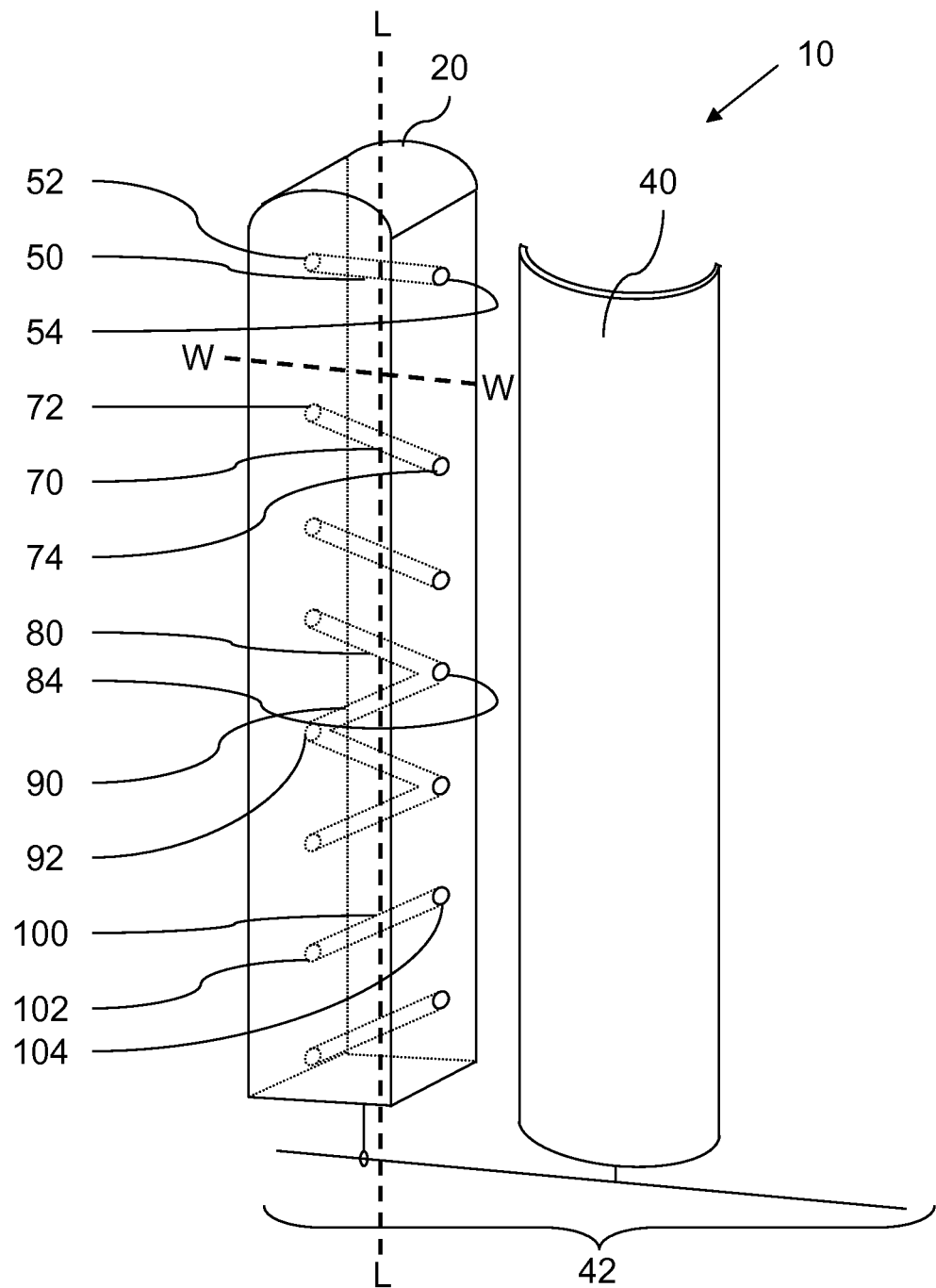

FIG. 1 shows one exemplary embodiment of a suture guide 10. In this embodiment, the suture guide includes a tissue guard 40 and a flanking post 20. In the depicted embodiment, the tissue guard has a concave shape, and the concavity faces toward the back of the device. This shape can facilitate a snug contact between the guard and an underlying convex tissue. The guard may various degrees of concavity, from, for example, about 120 degrees of arc to about 180 degrees of arc. The guard may also have other shapes, including a flat plate, rounded corners, squared-off corners, v-shaped, and others. The free end of the guard (the tip) may be curved, tapered, rounded, and/or thinned, akin to the blades of a vaginal speculum, to facilitate sliding along tissue.

The flanking post is disposed to one side of the tissue guard. The post defines a plurality of channels 50, 70, 80, etc. that extend through the post's width, from external orifices 52, 72, 92, etc. to internal orifices 54, 74, 84, etc. The channels are positioned so that a needle passing through one of the channels will move in a plane that does not intersect the tissue guard. This detail is shown more clearly in FIGS. 6-10. When the device is positioned on a tissue, the needles will then pass through the tissue behind (FIG. 4) or in front (FIG. 5) of the guard without being obstructed by the guard. "Behind" and "front" in this sense refer to the guard as viewed in the figures. When a suture guide is positioned for an Achilles tendon repair, for example, the needles will pass anterior or posterior to the tissue guard, where "anterior" and "posterior" are defined with respect to the patient's anatomy.

Figure 7:
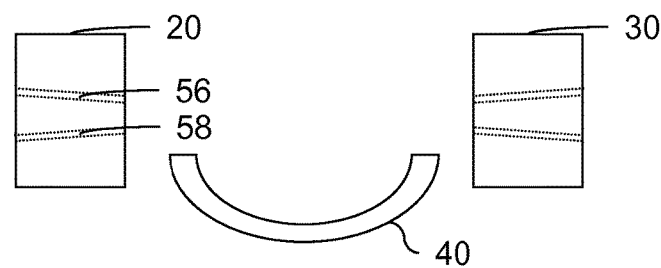

One or more of the channels may be parallel to the width of the flanking post, i.e., parallel to an axis W through the width of the post, to ensure that a needle passing through them will not intersect the tissue guard. However, one or more channels can be oriented non-parallel so that sutures passing through the tissue are in different planes and do not interfere with one another. The non-parallel channel should be so angled that its axis does not intersect the tissue guard. FIG. 7 shows one exemplary embodiment having non-parallel channels 56, 58.

One or more of the channels, exemplified here as channel 50, may be perpendicular to the long axis L of the flanking post in addition to being parallel to the post's width. This channel can define a horizontal suture needle guide path. (The path does not appear horizontal in the drawing due to the perspective.) At least one other channel, such as channel 70, is not perpendicular to the post's long axis, although it is still parallel to the width. This channel defines an oblique suture needle guide path. Some of the oblique channels may run in a first non-perpendicular direction, such as channels 70 and 80, while other oblique channel may run in a second non-perpendicular direction different from the first direction, such as channels 90 and 100. Adjacent oblique channels running in different directions can share a common orifice, such as orifice 84 shared by channels 80 and 90. It should be noted that the depicted post embodiment defines nine channels, but alternative embodiments may have more or fewer channels in accordance with particular applications.

In this embodiment, the post and the tissue guard are connected to one another by a rod 42. The guard can be affixed to the connector, while the post can be clampable and repositionable. For example, the post could be clamped in the illustrated position during part of a suturing procedure, then moved to the other side of the rod during another part of the procedure. A sliding arrangement can also allow the post to be positioned an appropriate distance from the tissue guard for a given tissue size or to accommodate the local anatomy.

Figure 2:
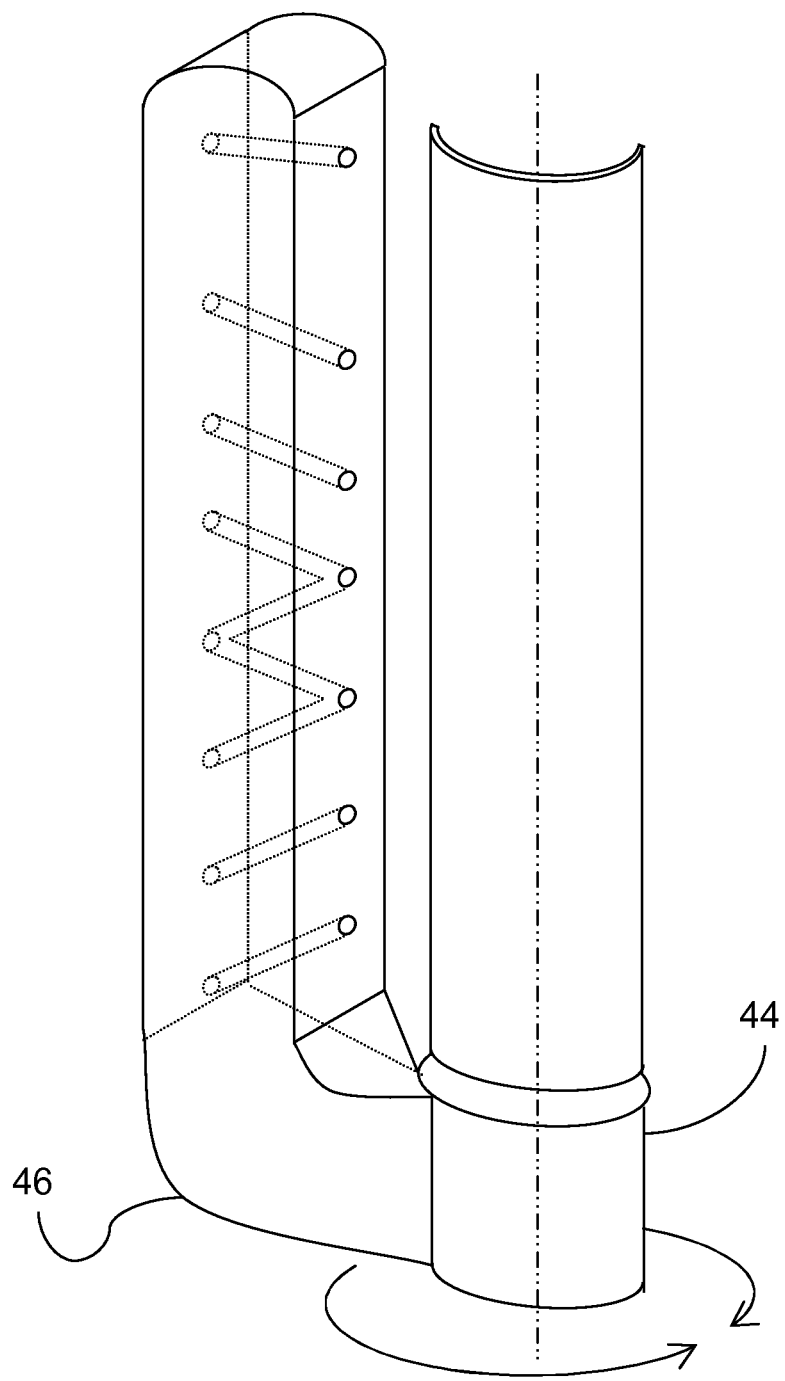

FIG. 2 shows another embodiment of a suture guide similar to the embodiment of FIG. 1, except that instead of a connecting rod, the guide has a shaft 44 to which the post is rotatably mounted by arm 46. The post can rotate about the shaft and thereby swing from one side of the guard to the other side. The post and/or shaft can include a mechanism to help ensure that the post is rotated into an appropriate position, i.e., one in which the tissue guard will not obstruct needles passing through the channels. Examples of appropriate mechanisms include a paired notch and detent, a stop, a clasp, a clamp, and alignment markings on the post and/or shaft to guide the user. The tissue guard may also be rotatable about the shaft, so that it can be swiveled between an anterior position and a posterior position.

Figure 3:
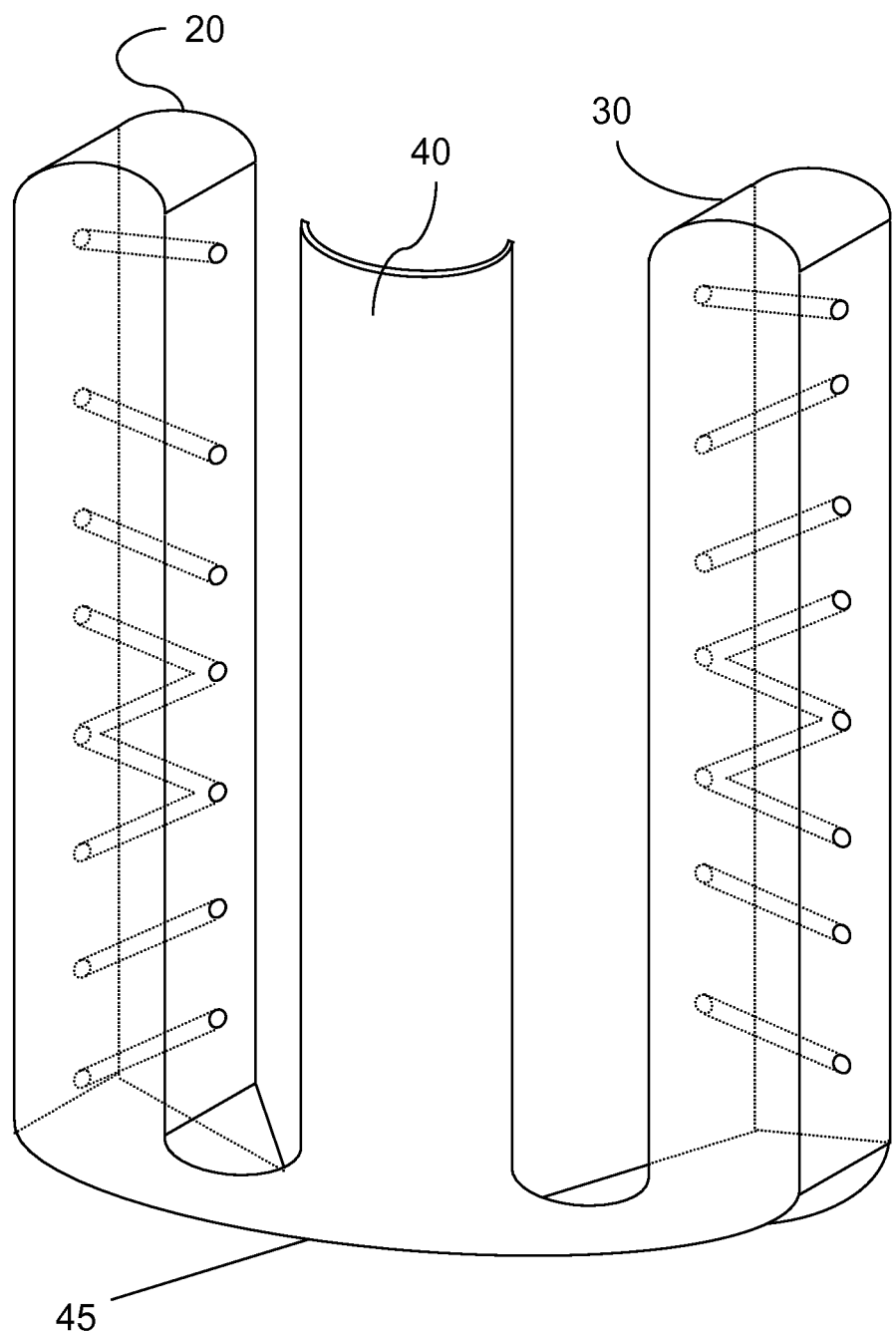
Figure 20:
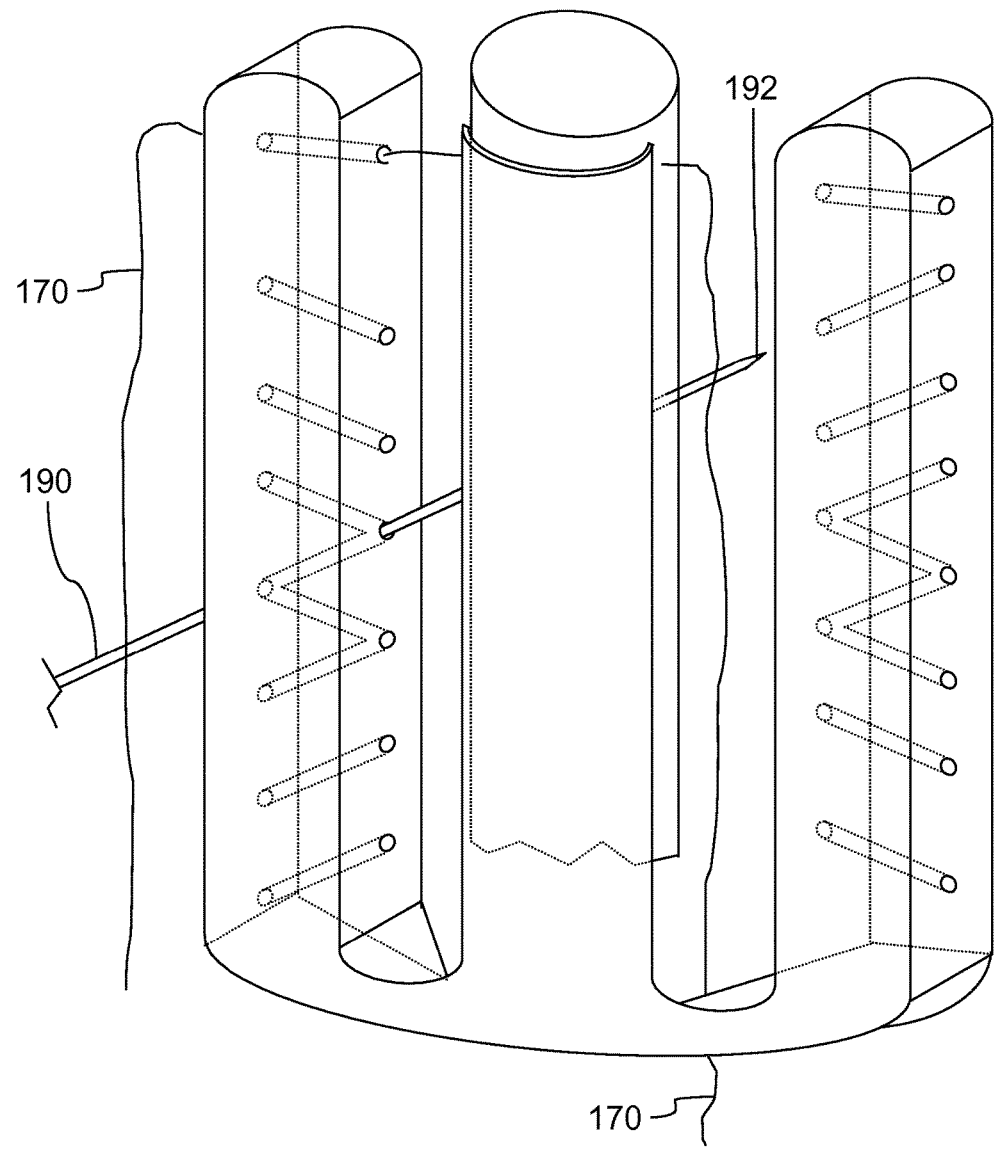
Figure 21:
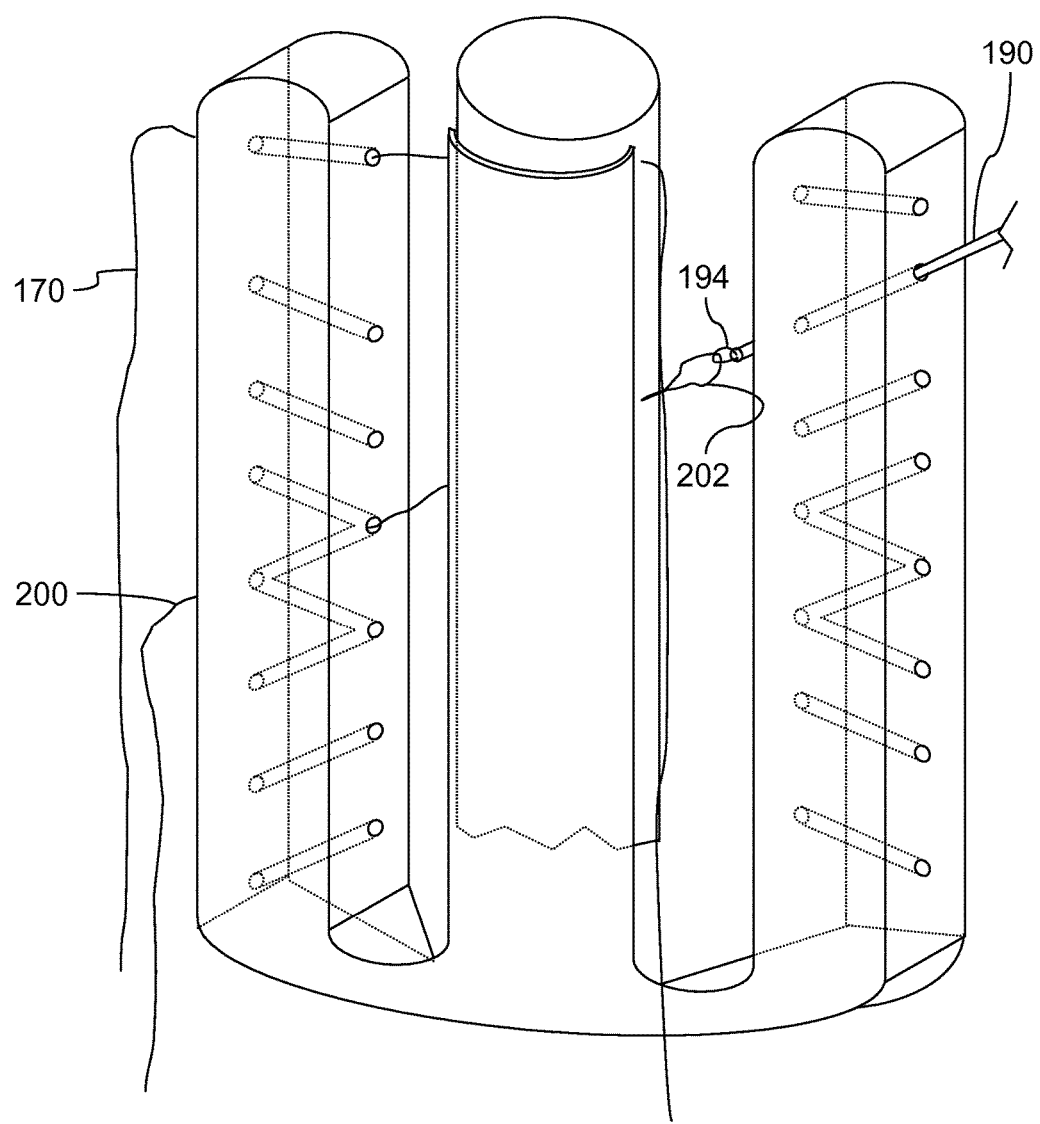
Figure 22:
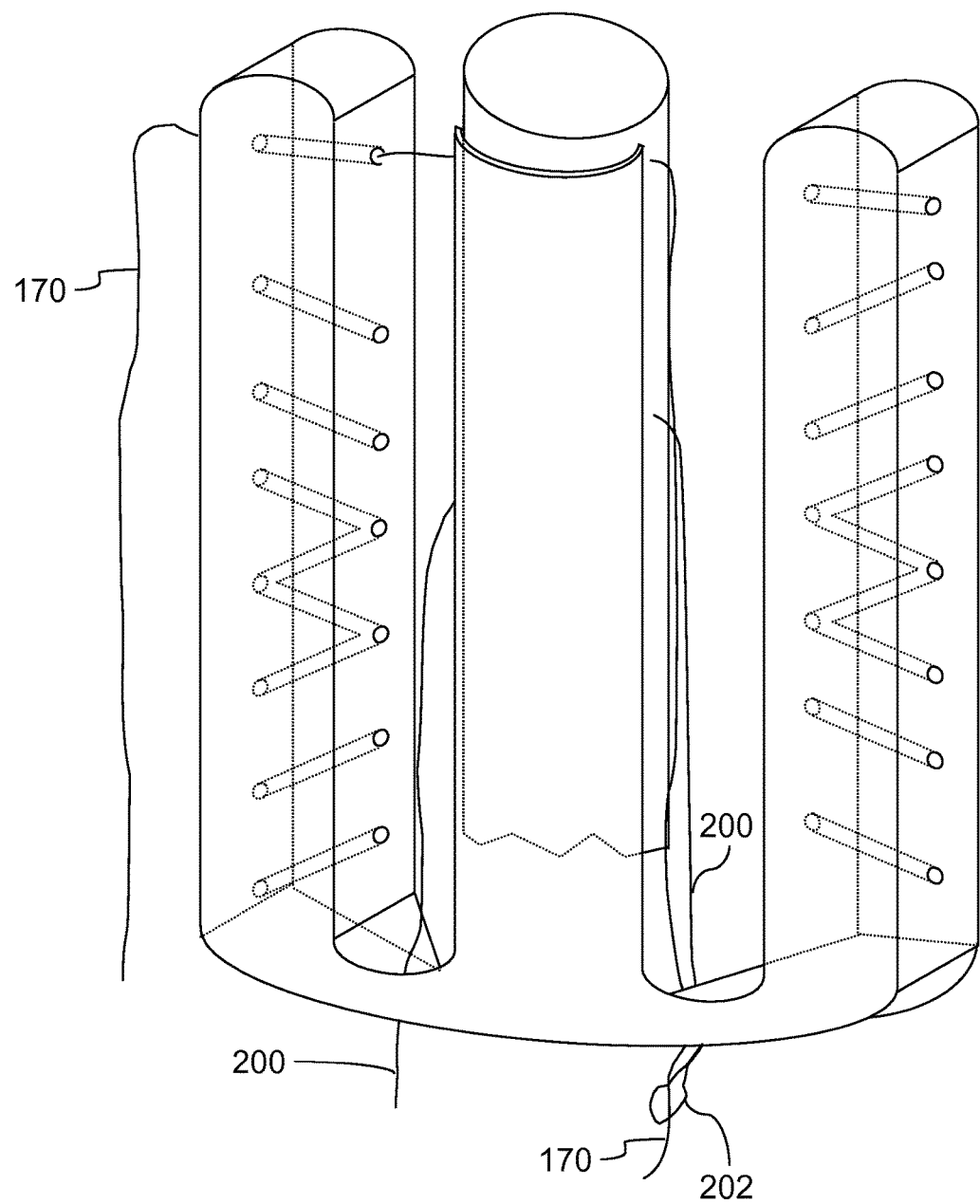

FIG. 3 shows yet another embodiment of a suture guide which includes a second flanking post 30 disposed to the side of the guard opposite from that of the first flanking post. The second flanking post, as illustrated, is a mirror image of the first post and includes a plurality of channels that complement the channels of the first post. It is preferred that the channels are so aligned that a needle passing through a channel in the first post will glide smoothly into a similarly-directed channel in the second post. An example of this is shown in FIGS. 20-21. In the embodiment depicted in FIG. 3, the posts are connected to the guard by a base 45. The base, guard, and post or posts can be of unitary construction. Alternatively, the parts could be connected by an adjustable connector as described earlier, such as a rod/clamp, or a bolt/screw arrangement, so that the posts may be positioned on either side of the guard in the optimal positions for a given use.

The disclosed suture guides can also be so positioned that the tissue guard supports tissue rather than covers it. This can be done by turning the device over and slipping the guard behind the tissue to be sutured. The guard would help hold the tissue to be sutured away from surrounding tissue and would also protect tissue deep to the tissue to be sutured.

Figure 6:
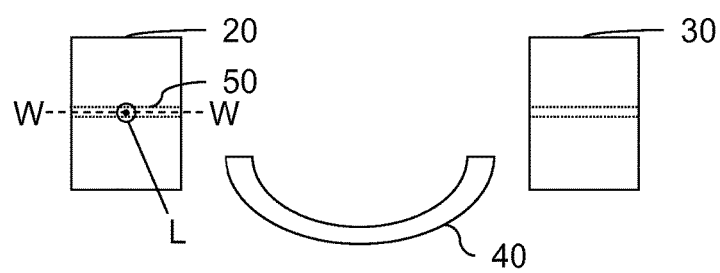
FIGS. 6-8B show top plan views of exemplary embodiments of suture guides.
Figure 8:
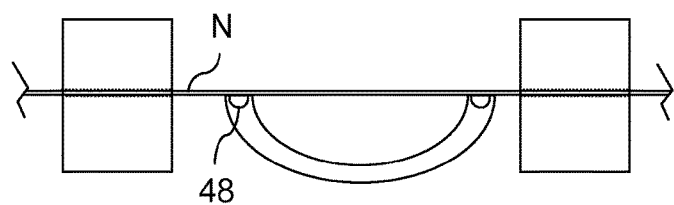

FIGS. 6-10 show additional views of various suture guide embodiments to depict certain features more clearly. FIG. 6 is a transverse cross section of the FIG. 3 embodiment taken at the level of channel 50 and projected upward. Width axis W and long axis L are depicted. Tissue guard 40 is positioned so that the suture needle guide paths are situated in one or more planes behind the guard, so that needles advanced through those paths will enter tissue held behind the guard during use. The guard does not extend so far back as to block the needle path planes, as this would interfere with suturing. However, as shown in FIG. 8, the guard may extend backward just up to the foremost guide plane, so that the edge of the guard may further assist needle N guidance. FIG. 8 also shows an alternative embodiment of guard 40, in which the edges of the guard define grooves 48 that may be used to slide suture catches up and down the guard. This feature will be described in more detail with reference to FIG. 19.

Figure 8A:
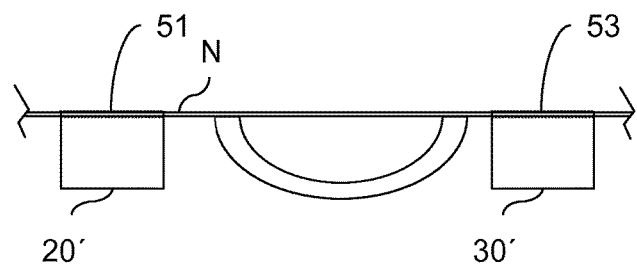
Figure 8B:
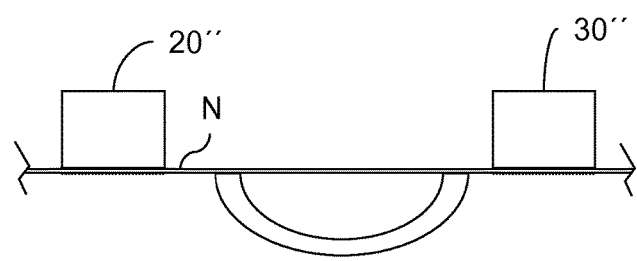

FIGS. 8A-B show alternative embodiments in which channels are replaced with grooves formed on the post surfaces. In FIG. 8A, posts 20' and 30' have less depth than in other embodiments and define grooves 51 and 53, respectively. Needle N slides in the grooves. The tissue guard is shown as coming up to the plane of the needle's passage, but this need not be so. FIG. 8B shows another embodiment of a suture guide have grooves instead of channels in posts 20"

and 30". In some embodiments, the post or posts do not define channels or grooves; instead, the post surface provides a planar needle guide.

Figure 9:
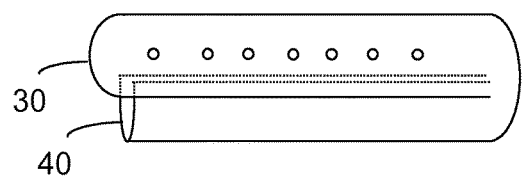
FIGS. 9-10 and 14-15 show side elevation views of exemplary embodiments of suture guides.
Figure 10:
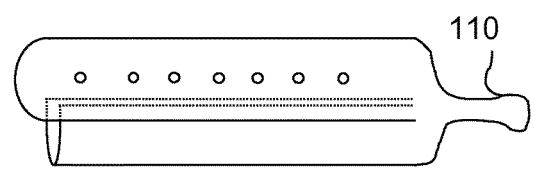
Figure 11:
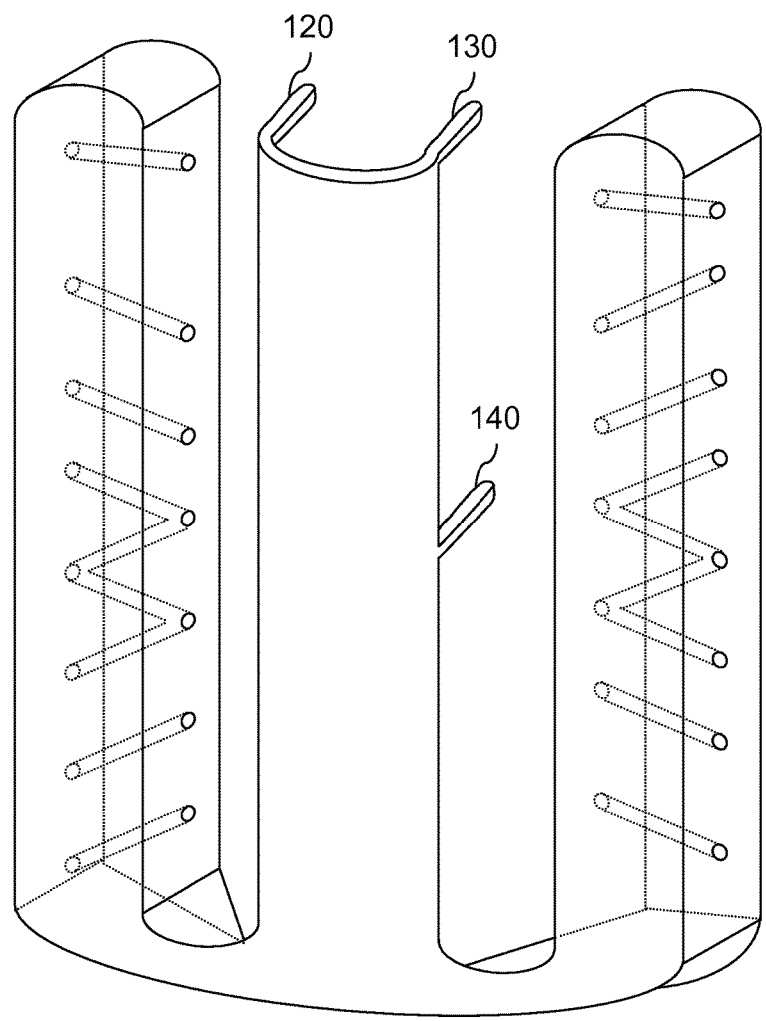

FIGS. 9-10 show side view of suture guides. FIG. 10, in particular, shows a suture guide with handle 110 to simplify the grip and positioning of the device.

FIGS. 11-15 show alternative embodiments of suture guides that include additional protuberances on the guard. The guard depicted in FIG. 11 includes catch receptacles 120 and 130. These protuberances prevent suture catches that are slid along the guard from advancing beyond the guard and potentially damaging tissue beyond the guard. In some embodiments, a guard may include a protuberance 140 disposed along the guard. A complementary guard on the other side of the guard is not visible in this perspective view, but is better seen as protuberance 150 in FIG. 15. The protuberances 140 and 150 help hold away body structures that are deeper than the tissue being sutured, to prevent the suture catch from inadvertently contacting the deep structure, and also to keep the deep structure away from the suture needle guide paths.

Figure 12:
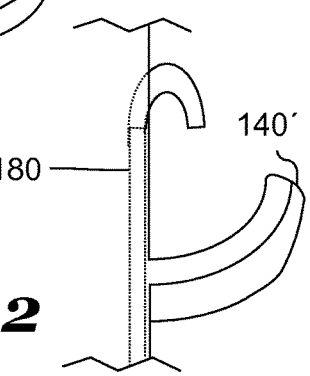
Figure 13:
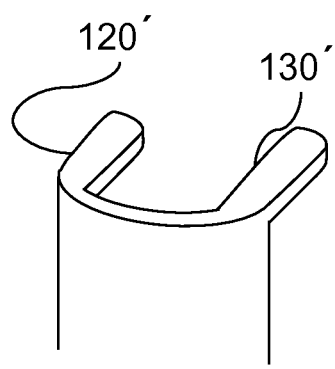
Figure 14:
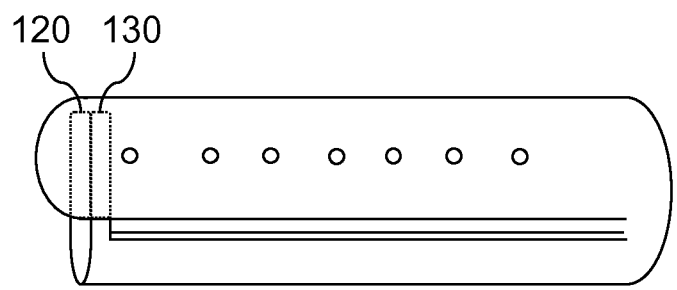
Figure 15:
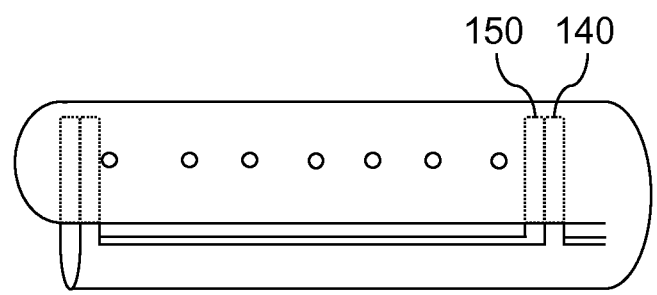

It is preferred that the mid-guard protuberances be so positioned that they do not cross the suture needle guide paths, so that they do not interfere with use of the device. It is also preferred that the mid-guard protuberances do not interfere with the movement of suture catches along the tissue guard. In some cases, as shown in FIG. 12, the protuberance 140' can be shaped so that its body is clear of the guard and suture catch 180 (discussed in more detail with reference to FIG. 19) can pass unimpeded. FIG. 13 shows detail of an alternate embodiment, in which the catch receptacles 120' and 130' are larger than the previous embodiment. The receptacles should be blunt, not sharp, so that they do not poke surrounding tissue. FIGS. 14 and 15 show side views of embodiments that include catch receptacles and/or mid-guard protuberances. (Note that, as shown in FIGS. 14-15, the sides of the tissue guard need not extend into the space between the posts as they do in FIGS. 6-7.)

Figure 16:
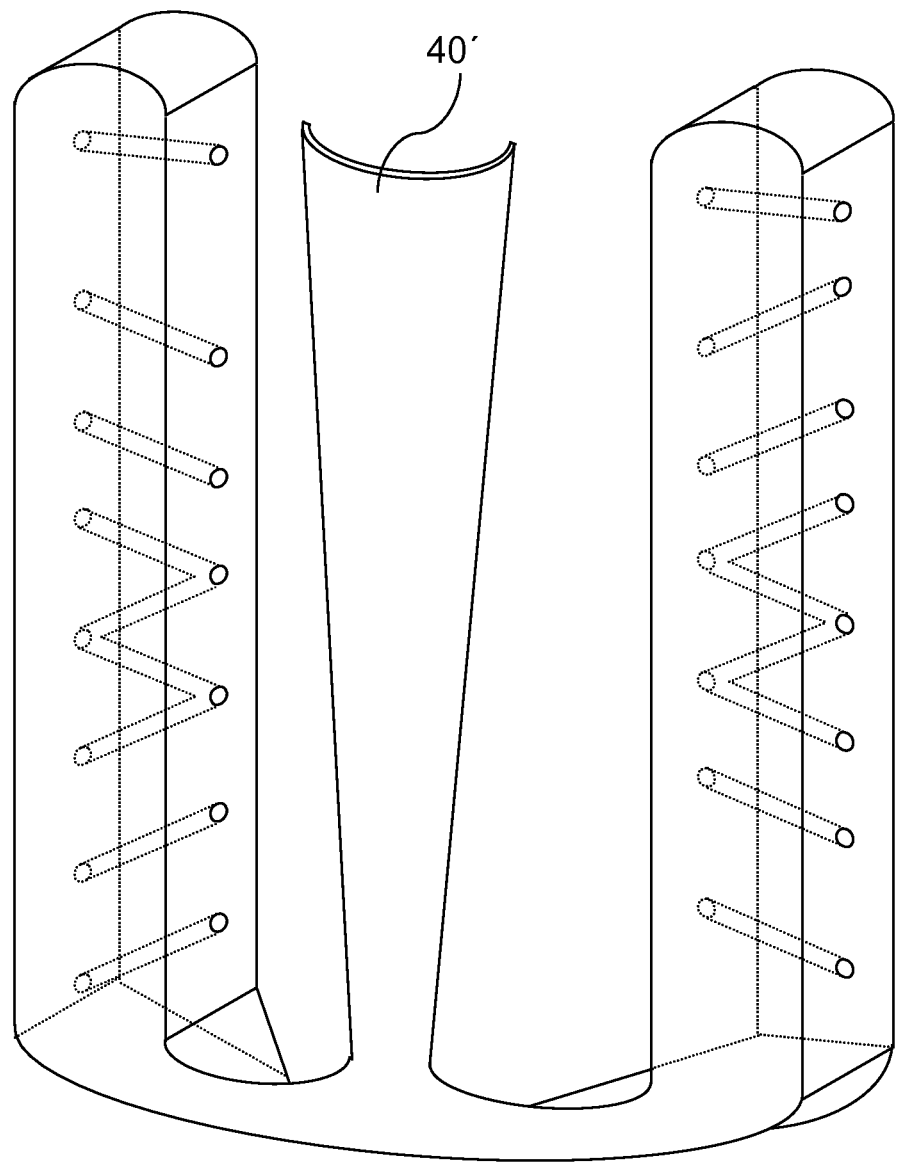

FIG. 16 shows another embodiment in which the guard 40' is tapered along its length. The guard may gradually narrow as it approaches the guide base. This tapered shape may be preferred when the device is used to suture a tendon or other tissue which itself has a tapered shape.

The suture guide can be formed from a variety of materials, including metals and plastics. A disposable, single-use device can be made from plastic and have a unitary design, so that it could be made by injection molding. A sterilizable, reusable device can be made from metal, such as stainless steel or other metals typically used in surgical applications.

Figure 17:
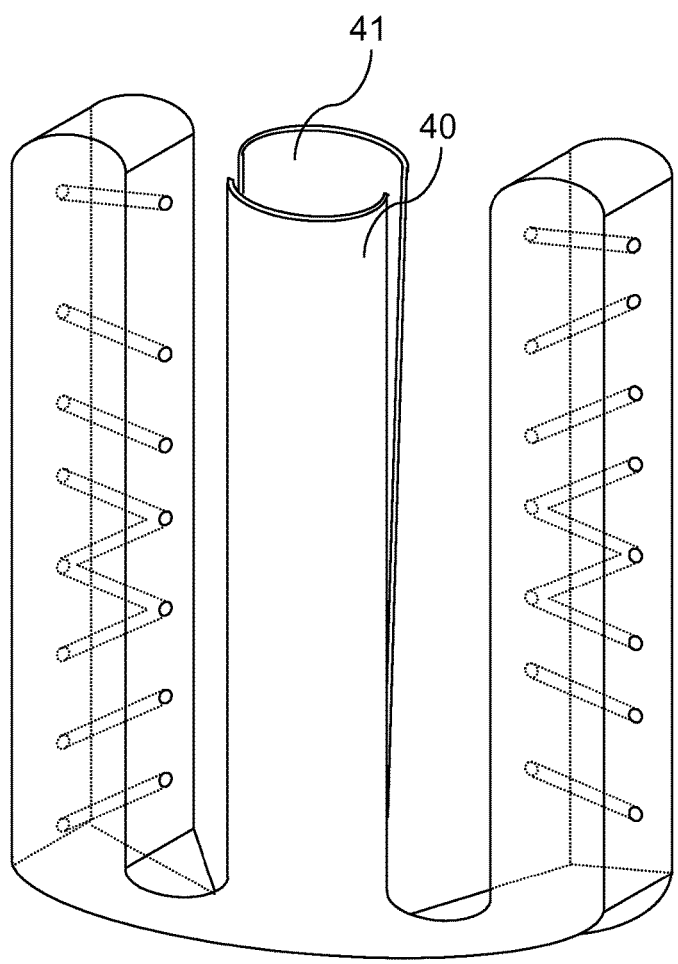
FIGS. 17-17A show perspective and elevation views, respectively, of another exemplary embodiment of a suture guide.
Figure 17A:
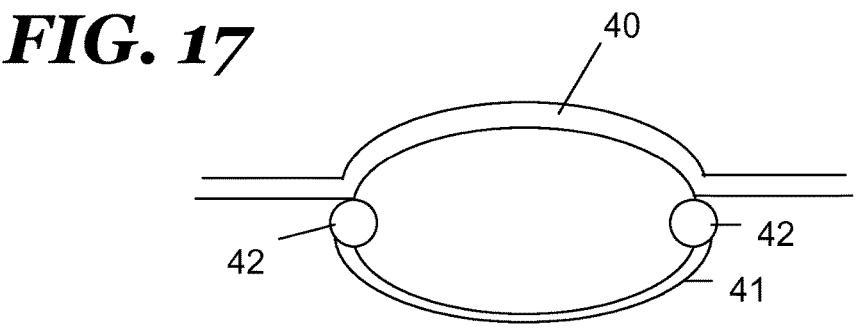

FIGS. 17-17A depict another embodiment of a suture guide, which includes a second tissue guard 41 pivotably coupled to the other tissue guard by hinges 42. The hinges may be lockable by, for example, a ratchet or a screw (not shown). The tips of the blades may be adapted for sliding along tissue, as disclosed above. The two guards permit simultaneous protection of tissues above and below the tissue being sutured using the suture guide. To position the double-guard device, the guards are swung to an open position, and the device is slid over the tissue like a sleeve. The guards can then be swung against the tissue and tightened, if desired.

EXAMPLES

FIGS. 18-34 describe, step-by-step, exemplary uses of suture guides. These examples depict the use of a suture guide having two posts, but the depicted uses can also be accomplished using a one-post suture guide, in which the device is flipped over, or the post repositioned, when maneuvers involving the second post are called for. These figures are schematic representations and are not necessarily depicted to scale; rather, they illustrate the principles of use. The end result of the exemplary uses is to have a suture threaded through the tissue in a crisscross pattern.

Figure 18:
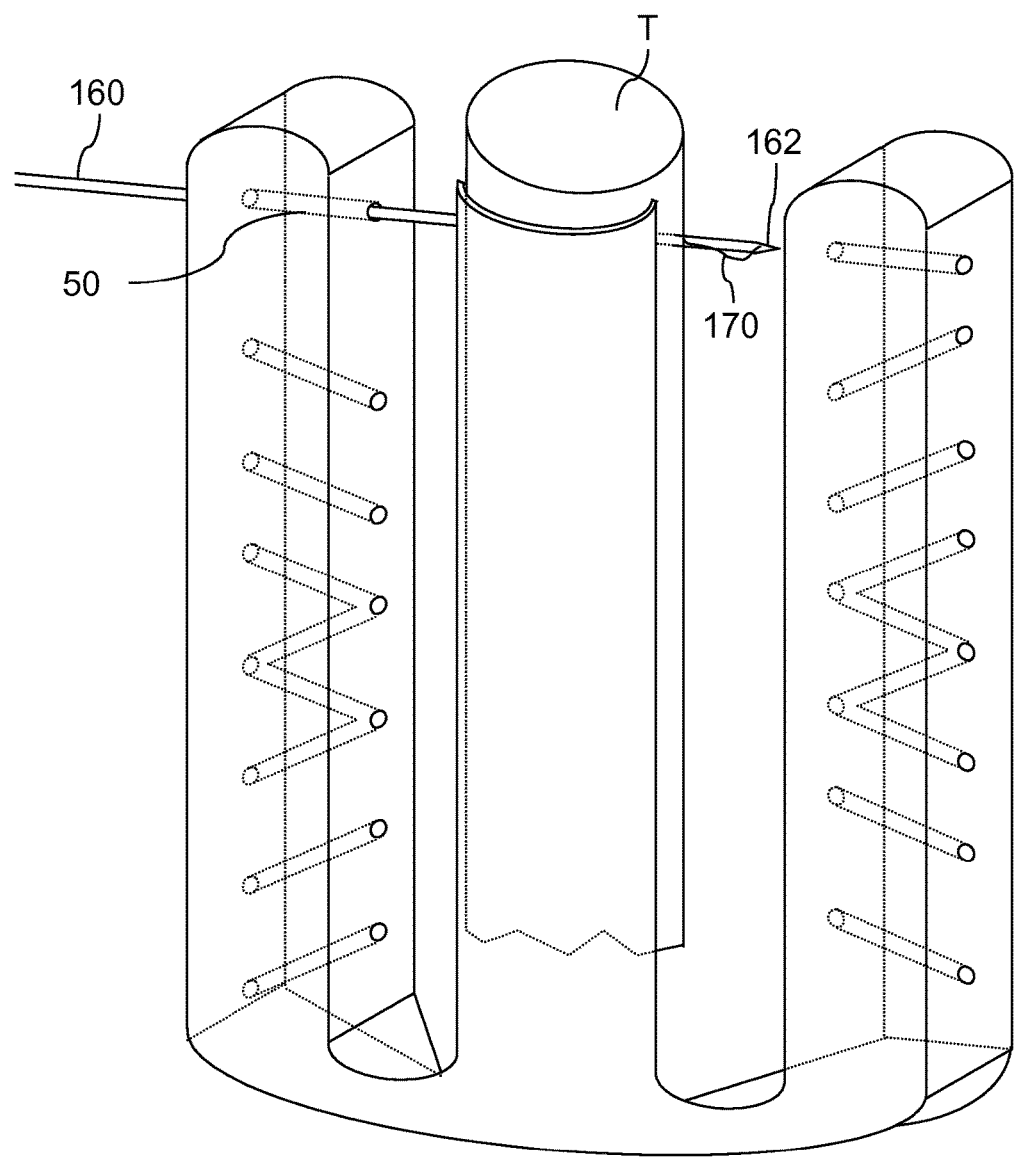

FIG. 18 shows the starting condition for an exemplary suturing procedure. The suture guide is placed over a tissue T to be sutured so that the guard covers the tissue and the flanking posts lie on either side of the tissue. (In another embodiment, a device could be turned over, so that the tissue guard supports the tissue.) A first needle 160 is advanced through the horizontal channel 50, emerges into the space between the posts, and then enters the tissue. The horizontal channel positions the needle for a horizontal trajectory through the tissue. The needle may have a sharp tip 162 to facilitate clean entry of the needle into the tissue. As the needle passes through the tissue, it forms a horizontal needle track. The needle 160 is loaded with a first suture 170; the suture is drawn through the horizontal track. Once the needle emerges on the far side of the tissue, the first suture is accessible on the second side of the tissue. (In alternate embodiments, the horizontal channel might not be used or might be omitted from the device.)

Figure 19:
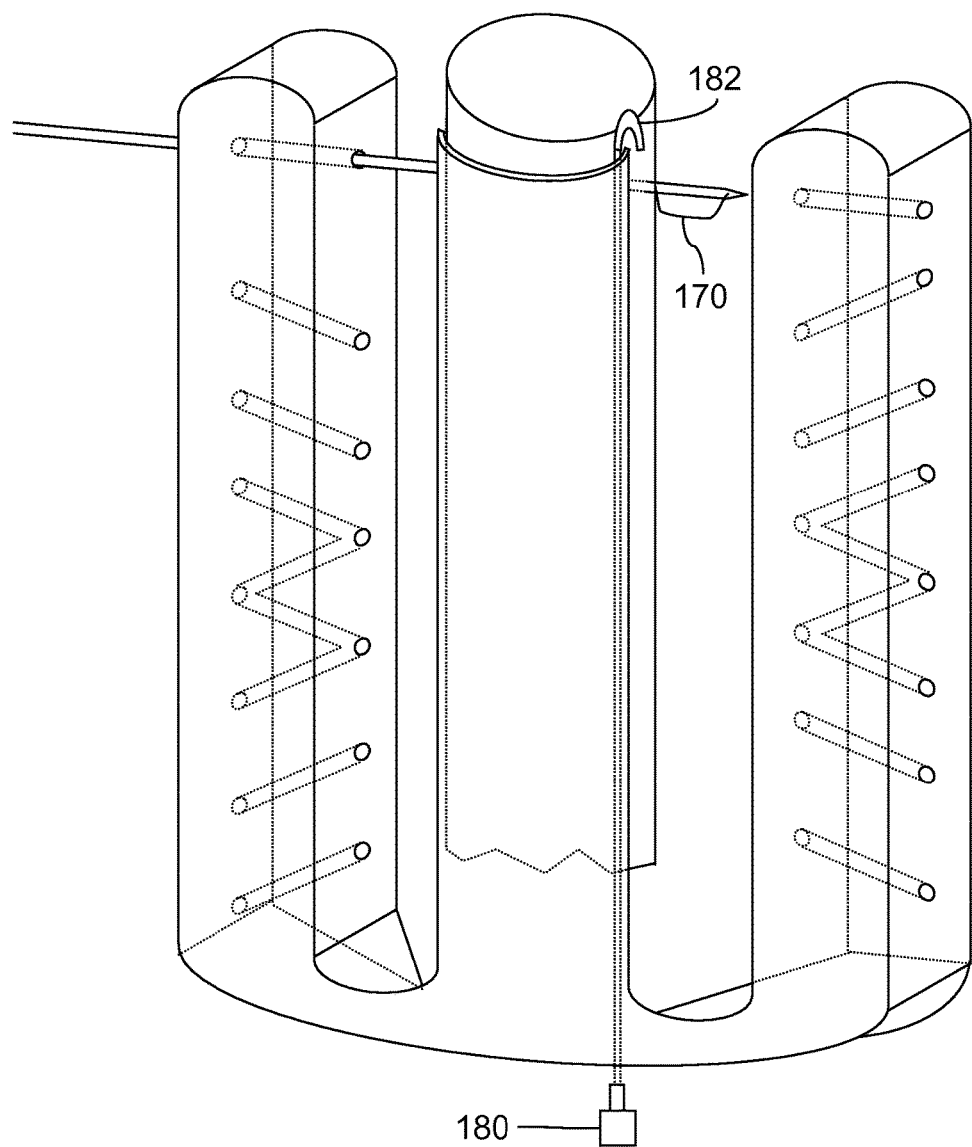

Next, shown in FIG. 19, a suture catch 180 may be advanced up through the guard. The catch may be guided up the suture through a groove, such as groove 48 (FIG. 8). The catch may have a hook 182 or similar structure to catch a suture. The hook may be curved to various extents. The hooks shown are curved through about 180 degrees, but hooks may be curved less, such as about 120 degrees, or may be curved more, such as through about 270 degrees, about 300 degrees, about 330 degrees, about 350 degrees, or about 360 degrees, so that the hook more resembles an eye or a loop. The hook is maneuvered to catch the suture (or may have been already placed in position before the passage of the first suture in FIG. 18), and then the catch is pulled down through the guard, taking the first suture with it. The catch may then be advanced again up through the guard to be in position for the next suture.

Figure 23:
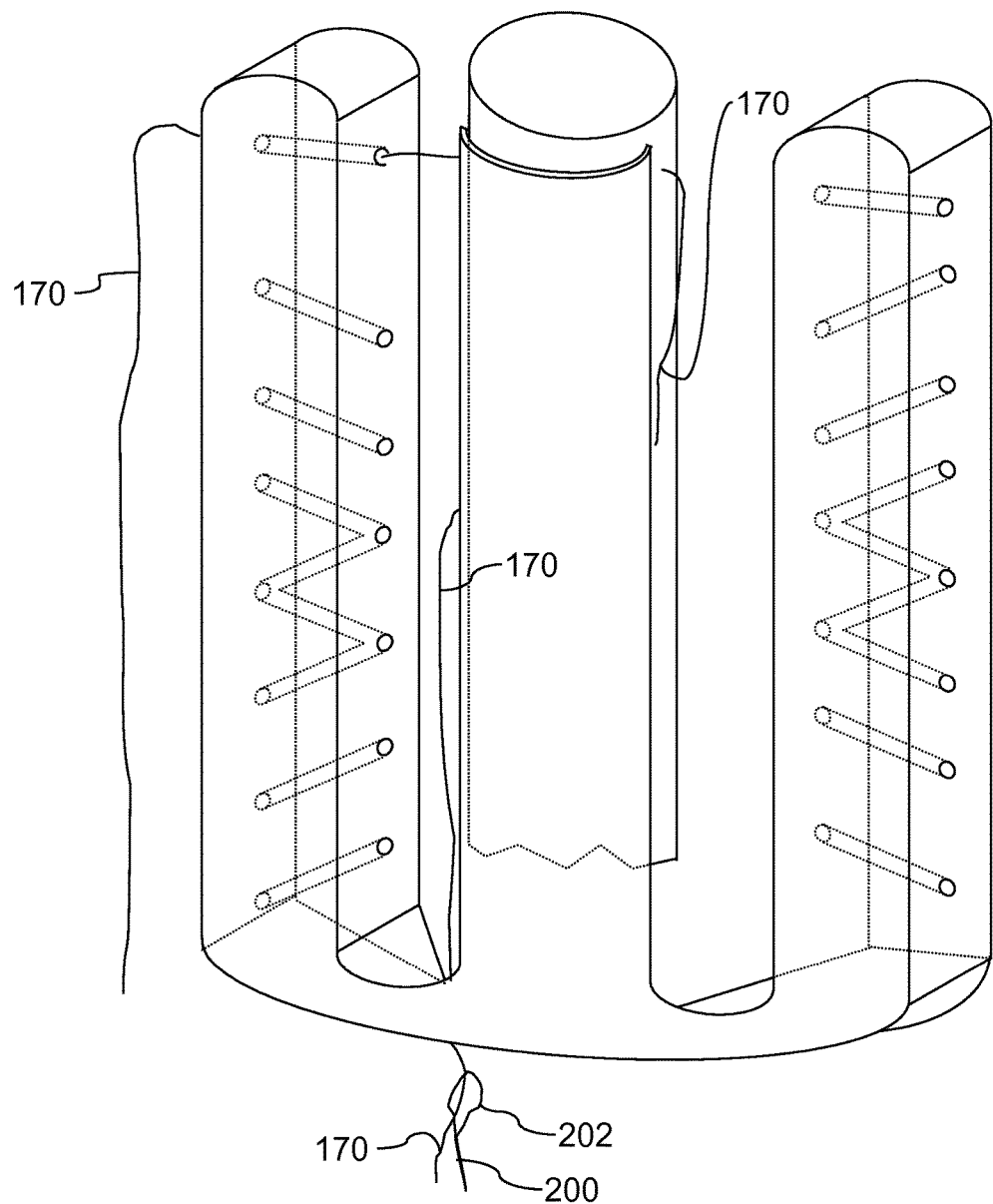

In FIG. 20, a second needle 190 is advanced through one of the oblique guide paths of the first post, into the tissue, out the far side of the tissue, and, optionally, into the corresponding channel in the second post. This motion forms an oblique track through the tissue. As shown in FIG. 21, a second suture 200 is attached to the back of the second needle. The second suture has a catch on its front end, such as a loop 202, and the second suture may be attached to the second needle by another loop 194 attached to the back of the needle. Once the front end of the second suture 200 emerges on the far side of the tissue, it is detached from the second needle, hooked by the suture catch 180 (FIG. 19), and brought down through the guard. The back end of the second suture protrudes from the first side of the tissue so that it can be grasped later. Next, shown in FIG. 22, the first suture 170 is threaded through the catch 202 on the second suture. In some embodiments, the catch could be tightened like a noose to grasp the first suture. Alternatively, the first and second sutures could be knotted or otherwise bonded. The back end of the second suture is then pulled so that the second suture is retracted back through the oblique track and pulls the first suture along with it. FIG. 23 shows the end of this step, with the first suture now making one horizontal pass through the tissue and one oblique pass. The distance between the exit point of the horizontal pass and the entry point of the oblique pass may vary; it is exaggerated in the drawing to show detail. In practice, such as during a repair of the Achilles tendon, the separation between the exit and entry points may be in the range of about 4 millimeters (mm) to about 26 mm, about 4 mm to about 12 mm, or about 5 mm to about 10 mm. In some embodiments, the separation is about 5 mm. The separation can vary depending on factors such as the size or consistency of the tissue to be sutured (for example, other tendons or other tissue types), the location or extent of the rupture, or the particular anatomy of the subject. The separation distance can be controlled, for example, by providing several suture needle guide paths from among which the user can select, or by instructing the user to reposition the suture guide.

Figure 24:
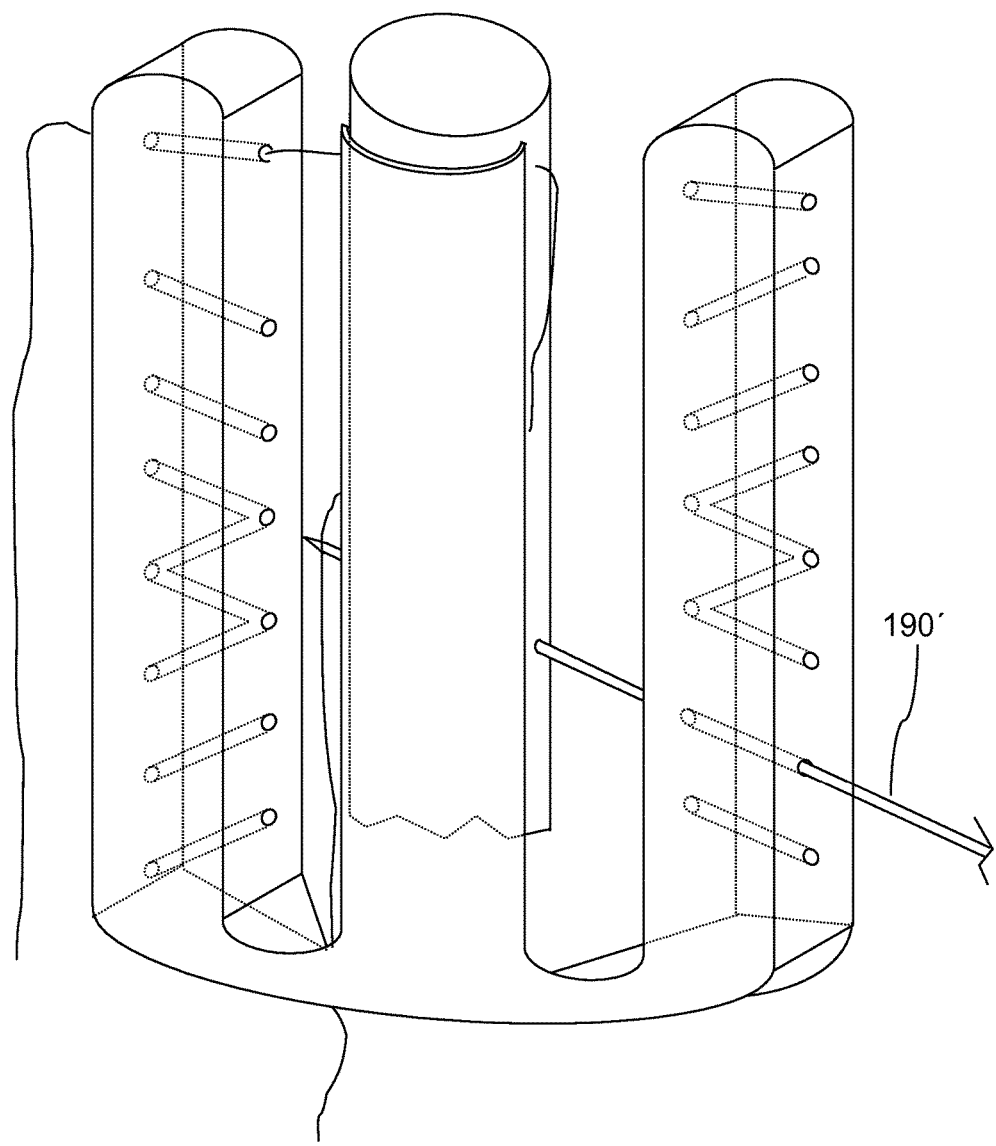
Figure 25:
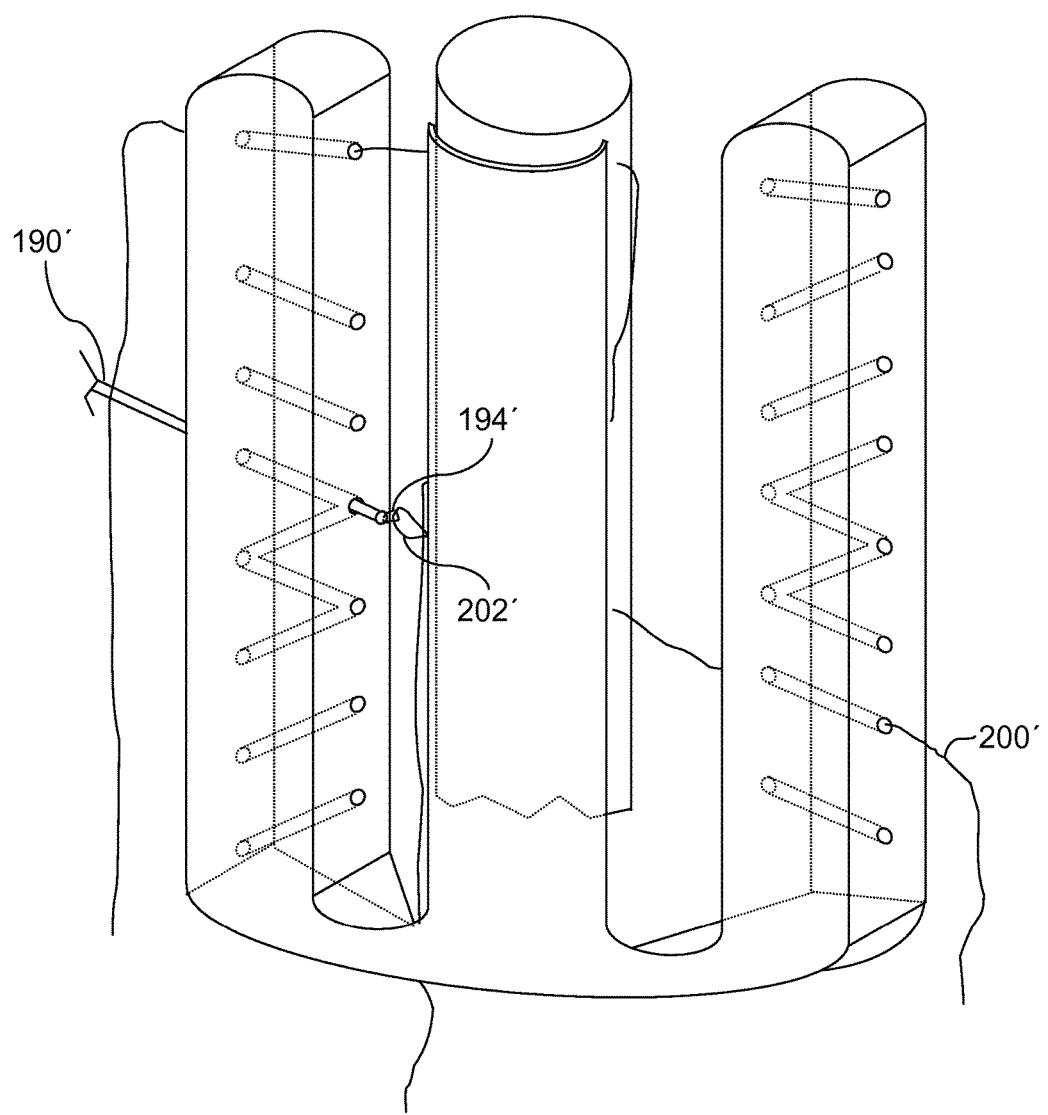
Figure 26:
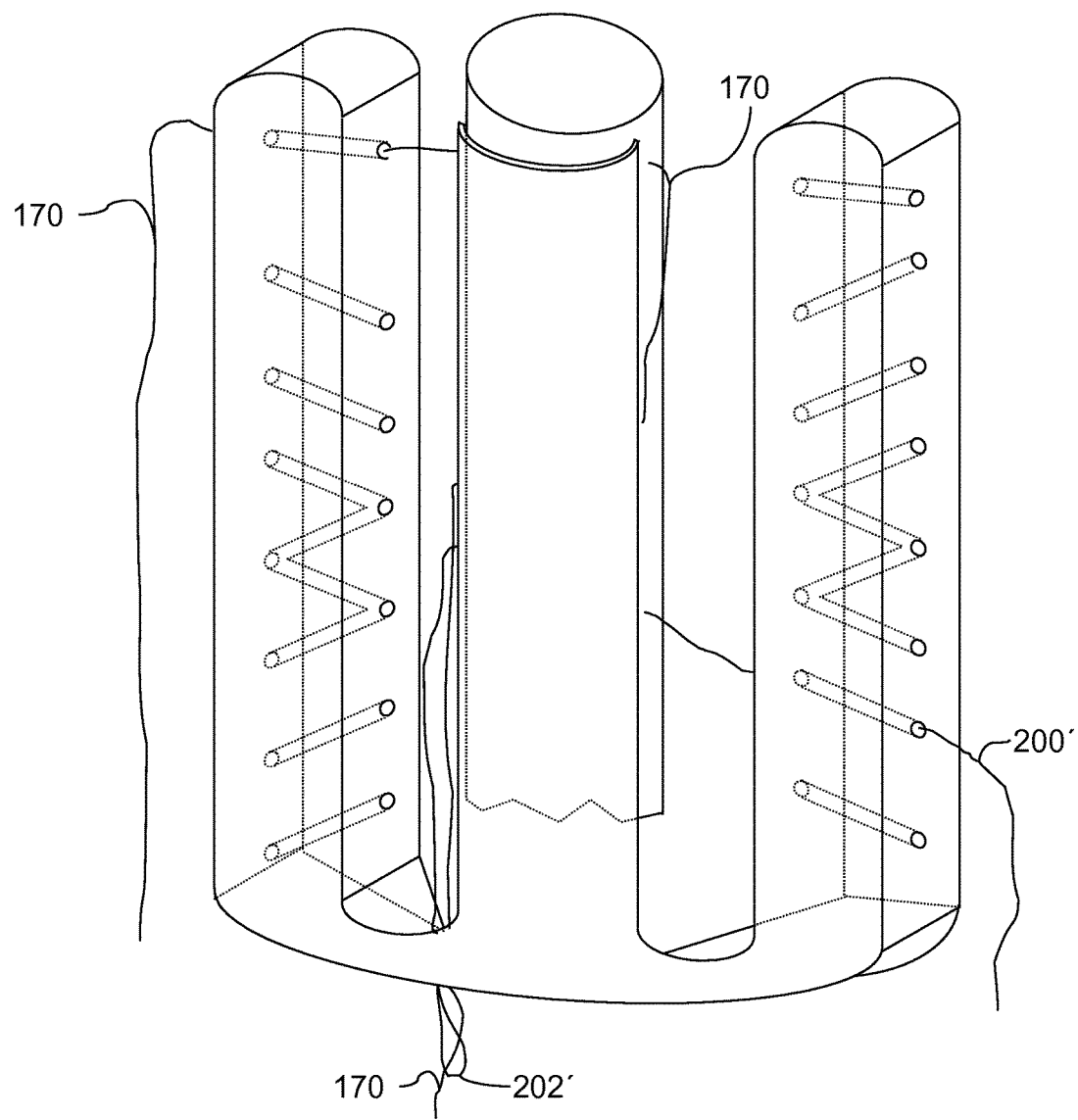
Figure 27:
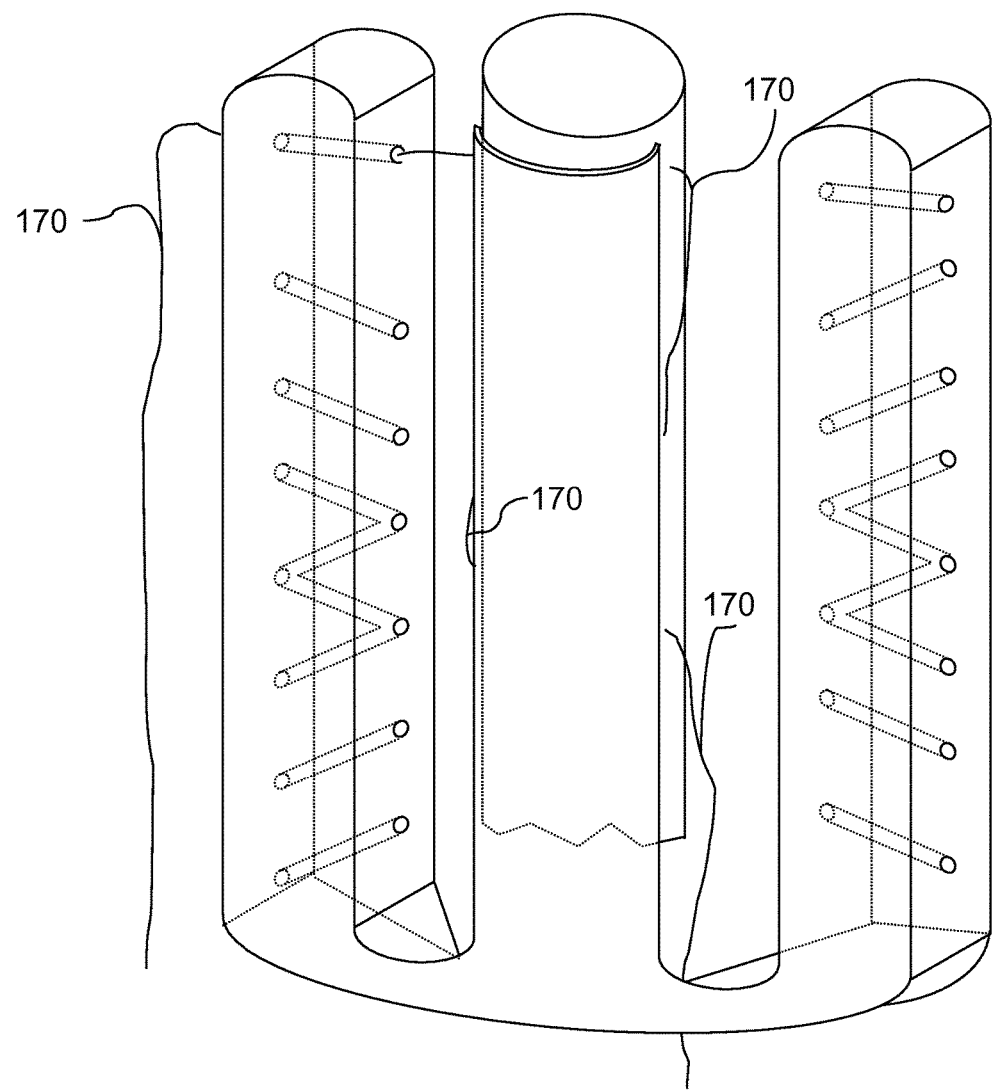

FIG. 24 shows the next step. The second needle is reloaded with the second suture or another suture. Alternatively, a third needle, with its own suture is provided. This needle 190' is advanced in an oblique channel from the other side of the tissue. If the suture guide has two posts, this channel would be in the second post. If the guide has one post, that post would be moved to the other side. This needle is advanced all the way through the tissue (FIG. 25), thereby forming a second oblique needle track, and brings its suture 200' out to the first side of the tissue. The suture 200' is detached from the needle by cutting link 194'. A suture catch is advanced along the guard to hook the suture and bring its catch 202' down, and, as shown in FIG. 26, the first suture 170 is threaded through it, as before. The suture 200' is then backed out through the second oblique needle track, pulling the first suture 170 with it. FIG. 27 shows the state of the procedure at this point: the first suture 170 has now made three passes through the tissue.

Figure 28:
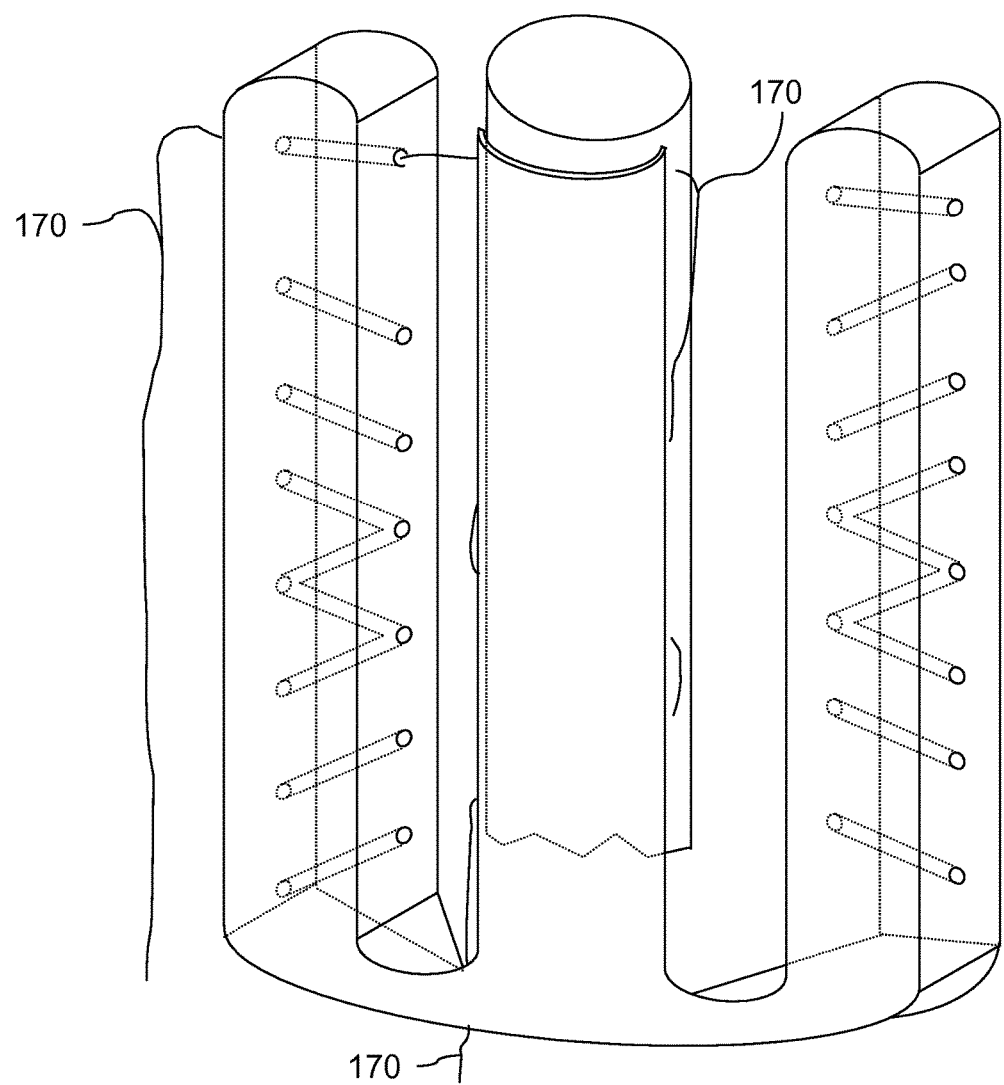
Figure 29:
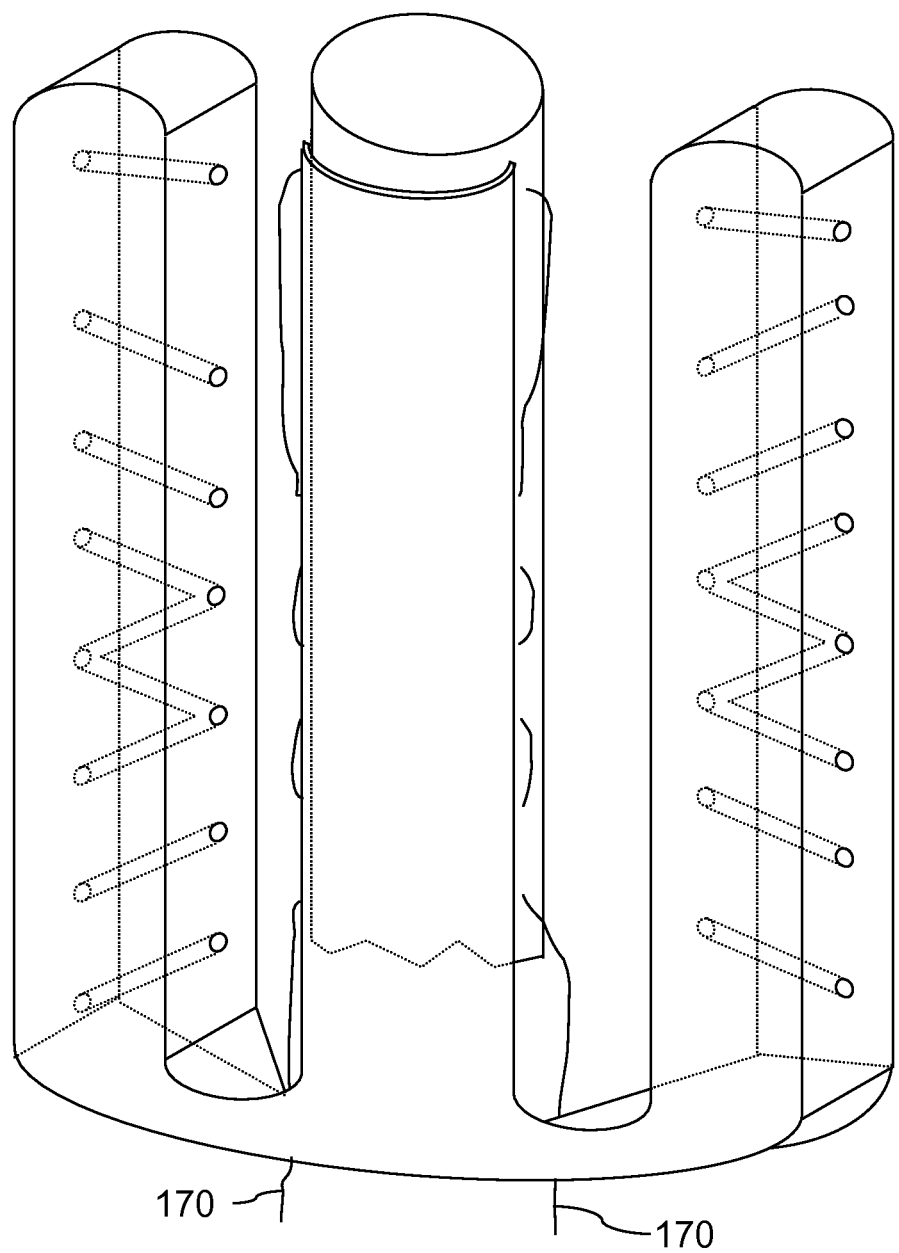
Figure 30:
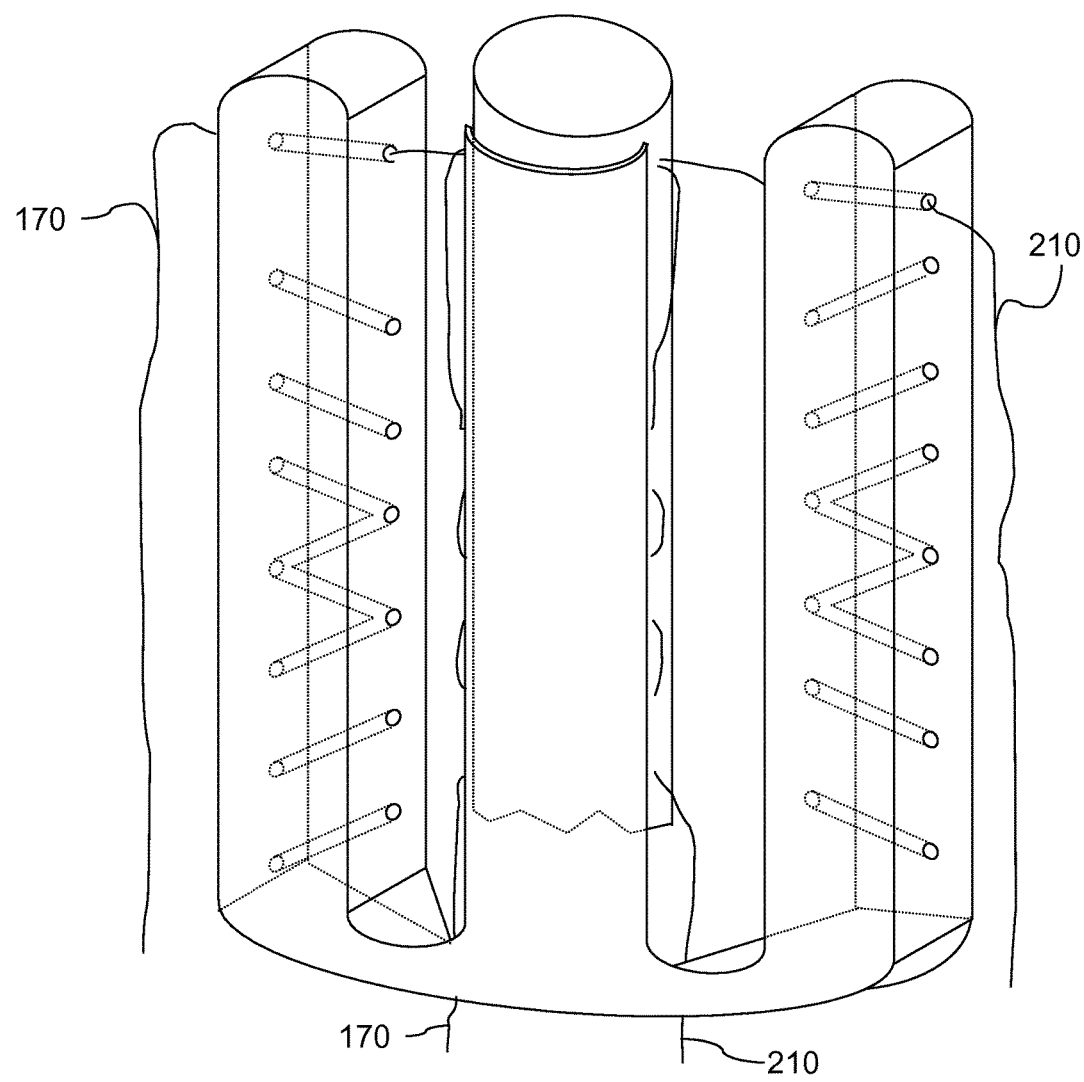

The process may be repeated one or more times to give the suture additional oblique passes through the tissue. FIG. 28 shows the conditional after one additional oblique pass is formed. The dangling end of the first suture 170 may be pulled into the space between the first post and the guard using a catch 180, and the entire procedure repeated, so that both ends of the first suture are stitched through the tissue in a crisscross pattern. The end result of this procedure is shown in FIG. 29. Alternatively, or in addition, a second suture 210, shown in FIG. 30, can be introduced through a channel in the second post (or relocated single post) and stitched through the tissue in mirror image to the first suture 170. As many additional sutures as desired can be placed in the tissue in this manner.

The entire process may then performed on the other end of the ruptured tissue, as shown in FIG. 31. In some embodiments, sutures could be passed through the other ruptured tissue end using conventional techniques. The free ends of sutures placed in each tissue end are pulled together and tied, as shown in FIG. 32, thereby completing the tissue repair.

A suture used in ruptured tissue repair may include an obstruction affixed to the suture. The obstruction may be so sized as to be unable to pass through needle and/or suture holes formed in the ruptured tissue when stitching the ruptured tissue as described herein. The obstruction may thus help prevent the suture from being pulled through the tendon. The obstruction may have a disk shape, such as suture button 220 shown in FIG. 33, an elliptical shape, a spherical shape, an oblong shape, or other shapes. The obstruction may be threaded onto the suture, at an appropriate point during a tissue repair, in such a way as to prevent the suture from sliding through the obstruction. The obstruction may have a shape complementary to the tissue against which it will nestle, such as a concave surface against a rounded tissue.

The obstruction may be made of a wide variety of materials, such as metals, biocompatible metals, polymers, biocompatible polymers, resorbable materials, biodegradable materials, and/or combinations of these. In the case of an obstruction made from a nonresorbable or nondegradable material having a disk, spherical, or other circular-type shape, the diameter may be in the range of about 1 mm to about 10 mm, about 3 mm to about 10 mm, about 3 mm to about 6 mm, or about 4 mm to about 6 mm. Other shapes may have a largest dimension in similar ranges. If the obstruction is made from a resorbable or degradable material, its size may be larger.

Figure 33:
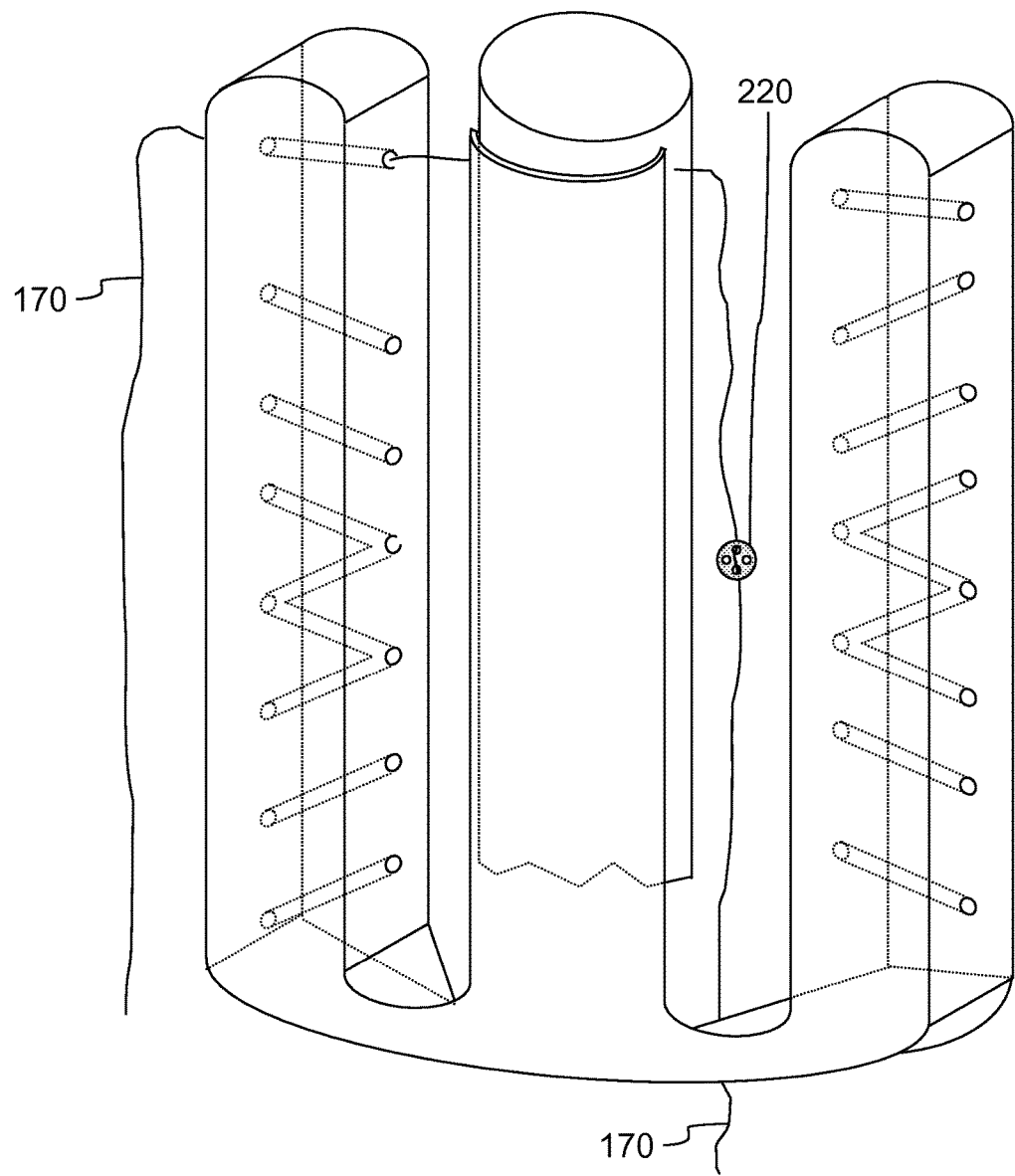
Figure 34:
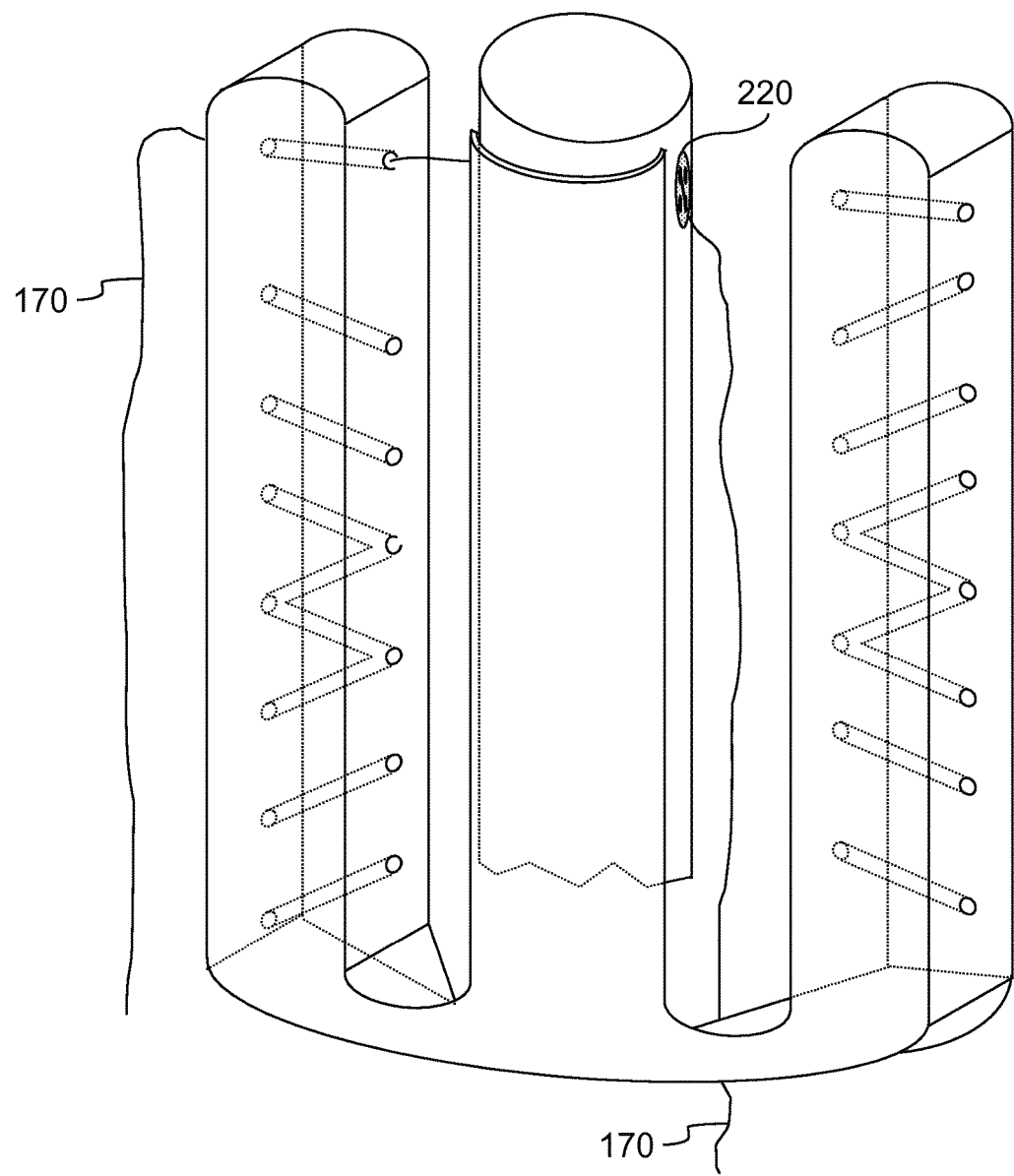

FIGS. 33-34 depict an exemplary use of an obstruction during a tissue repair. After a horizontal pass is made and the end of suture 170 is pulled through the tissue (the situation after that shown in FIG. 19 and before that shown in FIG. 20), the obstruction 220 may be threaded onto the suture (FIG. 33). The obstruction may be positioned on the suture at a location that leaves enough suture on either side to complete the diagonal stitches. The suture may be pulled back through the tissue to bring the obstruction snugly against the tissue (FIG. 34). The repair may then resume as shown in FIG. 20 et seq.

Figure 35:
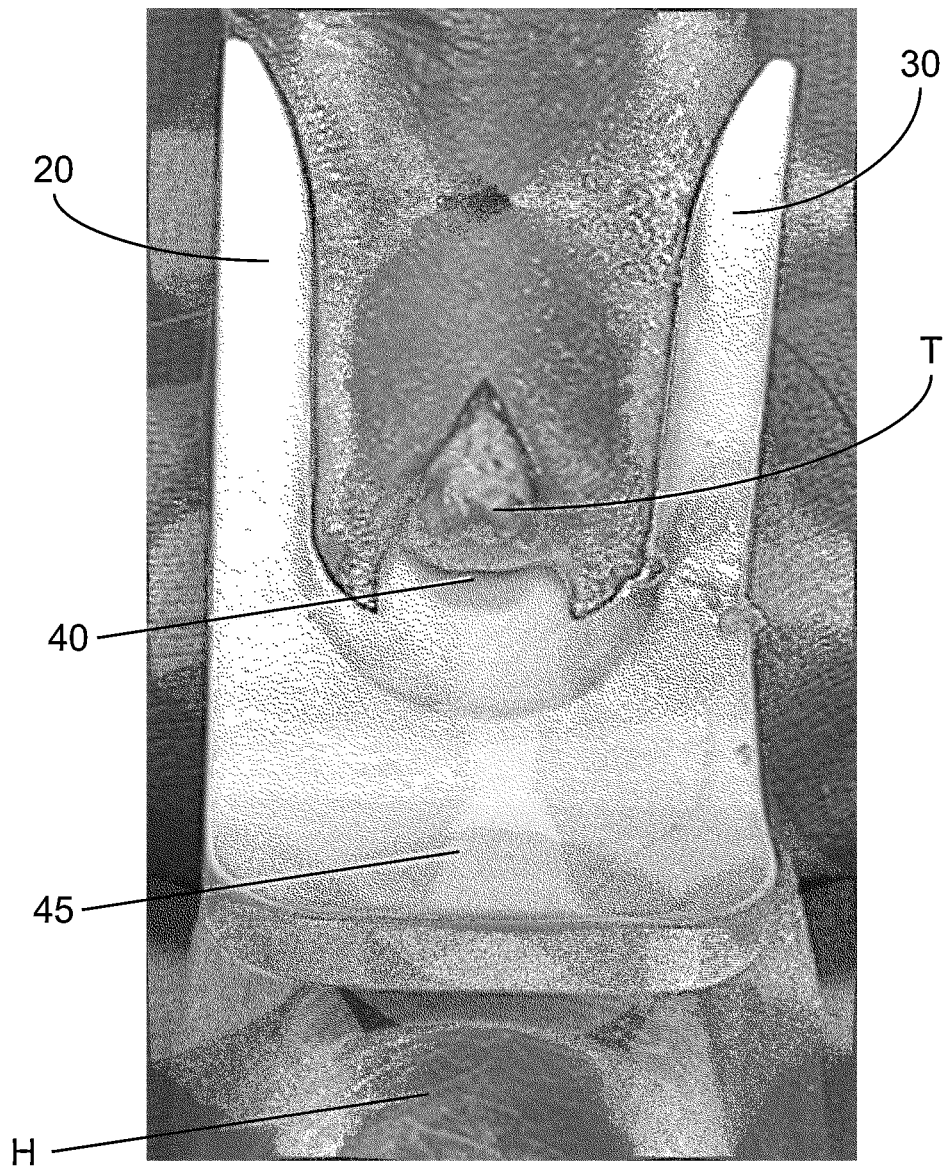
FIG. 35 is a photograph of an exemplary suture guide positioned on a subject for an Achilles tendon repair.

FIG. 35 is a photograph of an exemplary suture guide 10 in use for an Achilles tendon repair. The guide includes flanking posts 20, 30, tissue guard 40, and base 45. The guide is positioned superior to a subject's heel H. The flanking posts rest outside the skin on either side of a small incision that is made to reveal a portion of ruptured tendon T. The tissue guard in this exemplary use is slid in through the incision to rest below the ruptured tendon and protect underlying tissue. During the stitching process, a needle carrying a suture is advanced through the appropriate post, through the skin, through the tendon, then through the skin and the other post. After the suture is separated from the needle, its free end is pulled back through the post and the skin using a hook or similar structure described elsewhere in this disclosure.

Exemplary uses of the disclosed suture guides include Achilles tendon repair, anterior tibial tendon repair, repair of extensor tendons, flexor tendons to the fingers, tendons of the arm as well as other tendons and other tissue types.

A kit may include a suture guide disclosed herein and one or more needles threaded with suture. A kit may include an obstruction for affixing to a suture.

I claim:

1. A suture guide, comprising:
   a base;
   a tissue guard extending from the base; and
   a first flanking post and a second flanking post, the two flanking posts affixed to the base on opposite sides of the tissue guard, the posts extending from the base in parallel planes, each of the posts defining a plurality of channels passing through its width, the channels so oriented that, for each post:
   a) the channels define suture needle guide paths in one or more planes; and
   b) at least one channel is not perpendicular to a long axis of the first flanking post, so that it defines an oblique suture needle guide path;
   wherein the tissue guard is connected to the base by a connector so adjustable as to control spacing between the posts and the tissue guard; and
   wherein the guard and posts are so coupled to a shaft as to make the guard rotatable with respect to the posts.

2. The suture guide of claim 1, wherein the base and posts are of unitary construction.

3. The suture guide of claim 1, wherein the guard has a concave shape, and the concavity faces the suture needle guide paths.

4. The suture guide of claim 3, wherein the edges of the guard concavity extend to, but not into, a forward-most suture needle guide plane.

5. The suture guide of claim 1, wherein the guard has a cylindrical arc shape.

6. The suture guide of claim 1, wherein the guard tapers along its length.

7. The suture guide of claim 1, wherein the guard has a rounded free end.

8. The suture guide of claim 1, wherein the one or more planes in which the suture needle guide paths are defined do not intersect the tissue guard.

9. The suture guide of claim 1, wherein the first flanking post defines at least two channels that are not perpendicular to the long axis of the first flanking post.

10. The suture guide of claim 9, wherein at least two channels not perpendicular to the long axis of the first flanking post share a common orifice.

11. The suture guide of claim 1, wherein at least two channels that are not perpendicular to the long axis of the first flanking post extend through the first flanking post in directions different from one another.

12. The suture guide of claim 1, wherein at least one channel of the first flanking post is perpendicular to the long axis of the first flanking post so that it defines a horizontal suture needle guide path.

13. The suture guide of claim 12, wherein that flanking post defines at most one channel perpendicular to the long axis of the first flanking post.

14. The suture guide of claim 1, wherein all channels defined by either of the two flanking posts are not perpendicular to the long axis of the flanking post by which the channels are defined.

15. The suture guide of claim 1, wherein at least one channel of either the first flanking post or the second flanking post is parallel to the width of that flanking post.

16. The suture guide of claim 1, wherein at least one channel of either the first flanking post or the second flanking post is non-parallel to the width of that flanking post.

* * * * *